(12) United States Patent
Weiss et al.

(10) Patent No.: US 12,390,143 B2
(45) Date of Patent: **\*Aug. 19, 2025**

(54) SIGNAL PROCESSING METHOD FOR DISTINGUISHING AND CHARACTERIZING HIGH-FREQUENCY OSCILLATIONS

(71) Applicant: Thomas Jefferson University, Philadelphia, PA (US)

(72) Inventors: Shennan Weiss, Philadelphia, PA (US); Zachary Waldman, Philadelphia, PA (US); Inkyung Song, West Windsor, NJ (US)

(73) Assignee: Thomas Jefferson University, Philadelphia, PA (US)

( * ) Notice: Subject to any disclaimer, the term of this patent is extended or adjusted under 35 U.S.C. 154(b) by 313 days.

This patent is subject to a terminal disclaimer.

(21) Appl. No.: 17/965,975

(22) Filed: Oct. 14, 2022

(65) Prior Publication Data

US 2023/0240585 A1 Aug. 3, 2023

Related U.S. Application Data

(63) Continuation of application No. 16/464,923, filed as application No. PCT/US2017/064509 on Dec. 4, 2017, now Pat. No. 11,510,606.

(Continued)

(51) Int. Cl.
*A61B 5/374* (2021.01)
*A61B 5/00* (2006.01)
(Continued)

(52) U.S. Cl.
CPC ............ *A61B 5/374* (2021.01); *A61B 5/24* (2021.01); *A61B 5/291* (2021.01); *A61B 5/369* (2021.01);
(Continued)

(58) Field of Classification Search
CPC ........... A61B 5/374; A61B 5/24; A61B 5/291; A61B 5/369; A61B 5/4094; A61B 5/4836;
(Continued)

(56) References Cited

U.S. PATENT DOCUMENTS 5,850,022 A 12/1998 Vassiliou
5,850,622 A 12/1998 Vassiliou et al.
(Continued)

FOREIGN PATENT DOCUMENTS

WO 2009103108 8/2009
WO 2017143319 8/2017

OTHER PUBLICATIONS

Georgios Tzedakis et al., "The Importance of Neighborhood Scheme Selection in Agent-based Tumor Growth Modeling", Cancer Informatics, 2015: 14(S4).*

(Continued)

*Primary Examiner* — Alexander Satanovsky
(74) *Attorney, Agent, or Firm* — Cozen O'Connor

(57) ABSTRACT

A device and a signal processing method that can be used with a device to recognize and distinguish a physiological high-frequency oscillation (HFO) from a pathological high-frequency oscillation. The signal processing method detects a physiological HFO in the electrical brain signal one regimen of electrical or optogenetic brain stimulation can be triggered, alternatively if the method detects a pathological HFO associated with epilepsy a different regimen of electrical or optogenetic brain stimulation can be triggered. Thus, the signal processing method can be utilized in a closed loop brain stimulation device that serves the dual purpose of both enhancing memory encoding, consolidation, and recall, or improving cognition, and reducing the probability of a seizure in a patient with epilepsy.

8 Claims, 22 Drawing Sheets

Related U.S. Application Data

(60) Provisional application No. 62/429,461, filed on Dec. 2, 2016.

(51) Int. Cl.
*A61B 5/24* (2021.01)
*A61B 5/291* (2021.01)
*A61B 5/369* (2021.01)
*G06F 17/18* (2006.01)

(52) U.S. Cl.
CPC .......... *A61B 5/4094* (2013.01); *A61B 5/4836* (2013.01); *A61B 5/7203* (2013.01); *A61B 5/7225* (2013.01); *A61B 5/7264* (2013.01); *A61B 5/7282* (2013.01); *A61B 5/742* (2013.01); *G06F 17/18* (2013.01)

(58) Field of Classification Search
CPC ... A61B 5/7203; A61B 5/7225; A61B 5/7264; A61B 5/7282; A61B 5/742; G06F 17/18
See application file for complete search history.

(56) References Cited

U.S. PATENT DOCUMENTS

| | | |
|---|---|---|
| 7,610,095 B2 | 10/2009 | Naisberg |
| 9,326,698 B2 | 5/2016 | Blanco et al. |
| 2012/0245481 A1* | 9/2012 | Blanco ................. A61B 5/7264 600/544 |
| 2014/0257128 A1* | 9/2014 | Moxon ................. A61B 5/6868 607/45 |
| 2015/0099962 A1* | 4/2015 | Weiss .................... A61B 5/374 600/409 |
| 2016/0045127 A1 | 2/2016 | Stacey et al. |
| 2016/0331307 A1 | 11/2016 | Purdon et al. |
| 2017/0311870 A1 | 11/2017 | Bardakjian et al. |
| 2018/0000370 A1* | 1/2018 | Modur ................. A61B 5/4094 |

OTHER PUBLICATIONS

International Search Report and Written Opinion issued on Mar. 1, 2018 in International Application No. PCT/US2017/064509 filed Dec. 4, 2017.

Burnos et al. "Human Intracrania High Frequency Oscillations (HFOs) Detected by Automatic Time-Frequency Analysis." In: PLos Once, Apr. 10, 2014, 9(4): e94831.

Tzedakis et al. "The Importance of Neighborhood Scheme Selection in Agent-Based Tumor Growth Modeling." In: Cancer Inform., 2015, 14 (Suppl4): 67-81.

* cited by examiner

A. Ripples at the depth peak

B. Ripples at the depth trough

C₁. Ripples at the peak and trough

C₂. Ripples at the transition between peak and trough

D. Hypothesis: The phase angles of ripple coupling differ in SOZ and NSOZ

SIGNAL PROCESSING METHOD FOR DISTINGUISHING AND CHARACTERIZING HIGH-FREQUENCY OSCILLATIONS

CROSS-REFERENCE TO RELATED APPLICATIONS

This application is a continuation of U.S. patent application Ser. No. 16/464,923 filed May 29, 2019, which claims the benefit of International Patent Application No. PCT/US17/64509, filed Dec. 4, 2017, published as WO2018/102815, which claims benefit to U.S. Provisional Application Ser. No. 62/429,461, filed Dec. 2, 2016, the disclosure contents of which are hereby incorporated by reference in their entirety.

GOVERNMENT SUPPORT

This invention was made with government support through NIH NS094633 awarded by the National Institutes of Health. The Government has certain rights in the invention.

FIELD OF INVENTION

The present invention is generally related to devices and methods for characterizing high-frequency oscillations in the brain so as to recognize and distinguish signals associated with epileptic pathophysiological processes, and recognize and distinguish signals associated with memory and cognition.

BACKGROUND OF INVENTION

Epilepsies are a family of chronic neurological disorders in which clusters of nerve cells or neurons in the brain signal abnormally. These abnormal brain signals are often characterized by seizures, which are transient, recurrent perturbations of normal brain function. As a chronic condition, epilepsy affects about 1% of the population in the United States. Each year, an additional 125,000 Americans are diagnosed with epilepsy. Indeed, this prevalence will increase substantially in the near future largely due to the rapidly expanding number of elderly Americans, in whom the incidence of epilepsy is the highest. Uncontrolled epilepsy poses a significant burden to society due to associated healthcare costs and chronic under-unemployment of otherwise physically and mentally competent individuals, when it occurs in individuals of a working age.

Anti-epileptic drug (AED) treatment is the standard therapy for epilepsy. Unfortunately, AEDs in current therapeutic use display significant side effect profiles. Additionally, about one third of all patients remain unresponsive to currently available medications. The need for more effective treatments for phamacoresistant epilepsy was among the driving forces behind a recent White House-initiated 'Curing Epilepsy: Focus on the Future' ('Cure') Conference (March, 2000), which emphasized specific research directions and benchmarks for the development of effective and safe treatments for people with epilepsy. One of the more common forms of epilepsy in humans that is frequently resistant to current therapy is the mesial temporal lobe epilepsy syndrome, or limbic epilepsy, that originates from limbic structures such as the hippocampus and amygdala.

At the physiological level, seizure activity can involve the transient, simultaneous hypersynchronous activation of a large population of neurons, either in one focal area, or throughout the brain, depending on the type of epilepsy. Seizure symptoms can vary widely. Some people with seizures may stare blankly for a few seconds during a seizure, while others may twitch their arms, legs, or other body parts. Having a single seizure does not indicate epilepsy alone, as at least two or more unprovoked seizures are generally required for epilepsy diagnosis.

An alternative approach to controlling epilepsy with drugs is through the use of neuroprosthetic devices. For nearly thirty years, epileptologists have been studying macroscopic electroencephalographic (EEG) recordings from the scalp to obtain global and local measures of scalp potentials using a variety of linear, nonlinear, and dynamical computational measures. On the surface of the cortex, EEG grid electrodes have been used in the clinical setting to determine epileptic foci. However, this approach is limited in its evaluation on the gross or macro level, which may be limited in its reach, both for treatment and for understanding of the underlying disease in the patient.

In studies performed in vitro using recent advances in multi-site electrode technology, acute preparations of hippocampal recordings have generated the basic constructs of neuronal firing related to the epileptic condition. In conjunction with in vivo recordings in both humans and animals, physiologists are performing studies to infer the normal and bursting responses of single units in excised tissue. It is recognized that such recordings from acute and slice preparations have provided significant contributions to research in the epilepsy field; however they are limited by the loss of network input and output from the rest of the brain (slice), and inability to chronically spontaneously seize, as do human subjects with temporal lobe epilepsy.

Accordingly, recognition of certain neural pathways and of electrical significance has allowed for neuroprosthetic system development to treat epilepsy. The FDA has approved a seizure control system based on electrical stimulation of the vagus nerve. For example, a system marketed by Cyberonics, Inc. (Houston, Tex.). Another system, developed by Neuropace (Mountain View, Calif) delivers electrical stimulation to the brain by way of subdural strips upon detection of an electrical signal that occurs at the start of a seizure.

Despite these advances, effective neuroprosthetics capable of predicting or warning of impending seizures and delivering timely therapeutic intervention have not been developed. The hallmark of epilepsy is recurrent seizures that are unpredictable and debilitating. Methods of seizure prediction in real-time would have significant impact on patients' lives. Even a few minutes of warning would allow a person experiencing a seizure to stop driving or get out of a risky environment to seek safety. Efforts in this area been limited by a lack of electrophysiologic control parameters that can be used to accurately predict the onset of the epileptic state and to deliver therapeutic feedback to the affected neural structures. In currently available systems, overall patterns of neuronal activity associated with the onset of seizure are detected, and upon such detection, standardized therapy is delivered to the brain in the form of electrical stimulation. The delivered stimulation is of predetermined strength and duration, regardless of the strength or duration of the seizure. This lack of control results in delivery of an electrical stimulus that may either be insufficient or excessive, both with respect to duration and stimulus strength.

SUMMARY OF INVENTION

The invention is a device and a signal processing method that can be used with a device that can recognize and distinguish a physiological high-frequency oscillation (HFO) from a pathological high-frequency oscillation. The signal processing method can operate near real time, and can be utilized for closed loop brain stimulation. If the signal processing method detects a physiological HFO in the electrical brain signal one regimen of electrical or optogenetic brain stimulation can be triggered, alternatively if the method detects a pathological HFO associated with epilepsy a different regimen of electrical or optogenetic brain stimulation can be triggered. Thus, the signal processing method can be utilized to develop a closed loop brain stimulation device that serves the dual purpose of both enhancing memory encoding, consolidation, and recall, or improving cognition, and reducing the probability of a seizure in a patient with epilepsy.

An embodiment of the invention is directed towards a digital signal analysis method for distinguishing and characterizing high-frequency oscillations in electrical recordings of brain activity. The invention consists of a signal processing method that is executed as computer code in the programming language Matlab (Natick, MA). High-frequency oscillations are brief (20-200 msec) bursts of neurophysiological activity with a spectral content ranging between (80-200 Hz) ripples and (200-600 Hz) fast ripples. High-frequency oscillations (HFOs) are biomarkers of brain capable of generating epileptic seizures, but are also signals associated with cognition and memory. Distinguishing and characterizing HFOs in electrical signals of brain activity is important for physicians and scientists who study and treat epilepsy, cognition, and memory. The detection and characterization of high-frequency oscillations has several confounds that are resolved by this digital signal analysis method. These confounds include i) that digital filtering of sharp transients in brain activity can result in the generation and detection of false HFOs that cannot be discriminated from true HFOs, ii) that digital filtering of brain activity does not easily allow fast ripples (250-600 Hz) that co-occur with ripples (80-200 Hz) to be identified and distinguished as two distinct events, iii) that digital filtering of brain activity does not allow HFOs that co-occur with inter-ictal spikes to be easily identified and classified as a distinct HFO event subset, iv) that HFOs that are generated by healthy brain regions cannot be differentiated from HFOs that are generated by epileptogenic networks. Overcoming these confounds is important because, i) false HFOs are sometimes artefactual, and the properties of HFOs cannot be characterized without first excluding false HFOs, since false HFOs do not exhibit an oscillatory frequency, power, or duration, ii) fast-ripples have a higher specificity for epileptogenic regions than ripple oscillations and occur infrequently relative to ripple oscillations, iii) ripples that co-occur with inter-ictal spikes have a higher accuracy for epileptogenic regions, than ripples that co-occur with background EEG oscillations, iv) ripples that occur in the neocortex during sleep may be important in mediating memory consolidation, while other ripples that occur in the neocortex during sleep may be generated by epileptogenic networks prior to, or during seizures.

A embodiment of this invention is directed towards a signal processing method for identifying, quantifying, characterizing, and discriminating high-frequency oscillations associated with physiological processes involved in memory and cognition from high-frequency oscillations involved in epilepsy related processes, and triggering distinct regimens of environmental or brain stimulation based on this discrimination comprising:

(a) a computer processor; and
(b) a non-transitory computer-readable memory storing instructions executable by the computer processor;
(c) a digital output;
(d) wherein said instructions, when executed by the computer processor, perform steps comprising:
(i) applying a wavelet convolution to the electrical signals to generate a time-frequency representation of the power of the signal;
(ii) determining a region of this first time-frequency plot that exceeds a threshold; wherein if the threshold is not met no HFO is registered by the apparatus;
(iii) determining the topography of a second time-frequency plot temporally centered around suprathreshold region of the first time-frequency plot by identifying contours of isopower;
(iv) determining at least two vertices of each contour as a coordinates of time and frequency;
(v) determining which contours exceed a specified threshold, and excluding all other contours
(vi) determining each contour as open-loop or closed-loop based on the coordinates of the vertices;
(vii) determining groups of contours based on their open- or closed-loop classification, power level, and time-frequency coordinates;
(viii) determining an event boundary contour as the closed loop contour of lower isopower in the group that exceeds a threshold value;
(ix) determining new event boundary coordinates by generating a third time-frequency plot with a lower minimum frequency limit than the second time-frequency plot and recalculating the event contours and contour group, if the minimum frequency of the original boundary contour is below a predetermined threshold;
(x) determining a duration of the HFO event based on the event boundary contour;
(xi) determining a mean power of the HFO by calculating the mean power magnitude across all coordinate points of the time-frequency plot within the event boundary contour;
(xii) determining an amplitude-weighted mean frequency of the HFO even within the boundary contour;
(xiii) determining if there are open loop contours that begin and terminate at the upper frequency limit of the second time-frequency plot;
(xiv) determining if these open loop contours are representative of a second HFO event by calculating a fourth time-frequency plot in a higher frequency range, identifying the region of
(xv) greatest power that exceeds a threshold, defining contours of isopower, determining if these are open or closed loop contours, defining groups of contours, and determining the even boundary contour;
(xvi) applying a distinct wavelet convolution to the electrical signals to generate a time-frequency representation of the power of the signal in a frequency range less than the HFO to determine if the HFO event is superimposed on an inter-ictal discharge, or if an inter-ictal discharge has a superimposed HFO by performing a wavelet convolution to the electrical signals to generate a time-frequency representation of the power of the signal;
(xvii) determining the gradient plot of this TF plot;
(xviii) determining the borders of objects in the TF plot, and the gradient plot of the TF plot, discharges by binarizing the TF plot and its gradient using an appropriate threshold and applying Moore-neighbor tracing algorithm;

(xix) determining the volume of the objects in the TF plot, and the gradient plot of the TF plot, using trapezoidal surface integration within the object borders derived from the binarized TF plot to the unbinarized TF plot, and gradient plot of the TF plot;

(xx) determining if any of the objects are near the borders of the TF plot, or have a height-width ratio less than a threshold and excluding these object from further analysis;

(xxi) determining if an object is representative of an inter-ictal discharge by defining the object of greatest volume in the TF plot, and object of greatest volume in the gradient plot of the TF plot, and calculating if the volume of these objects exceeds pre-defined thresholds;

(xxii) filter the electrical signals recorded from multiple locations of a subject using an electrical sensing device to produce a low-frequency data stream to determine if the preferred phase angle of coupling between the HFO and bursts of slower oscillations;

(xxiii) transform the low-frequency data stream to produce a low-frequency instantaneous phase; and instantaneous amplitude;

(xxiv) determine the start and end times of oscillatory bursts by smoothing the instantaneous amplitude function and applying predetermined thresholds;

(xxv) determine if the HFO coincides with one or several oscillatory burst epochs;

(xxvi) determine a HFO phasor with a mean phase angle and vector strength value based on the low-frequency burst instantaneous phase and the mean HFO event power magnitude across the boundary counter;

(xxvii) determine an HFO duration, an HFO mean power, an HFO mean frequency, and HFO phasors for all HFO events defined in the electrical signals from multiple locations;

(xxviii) identify a location of the brain corresponding with the same electrical signals determined to displays HFOs of a predefined HFO duration, HFO mean power, HFO mean frequency, and HFO phasors based on where the electrical signals were recorded; and (xxix) generating a report of the identified location of the subject as a target for a therapeutic procedure for treating a cause of the identified HFO; wherein (xxx) for each classified high-frequency oscillation determine the probability that the event results from a physiological process involved with memory and cognition, or a pathophysiological process involved with epilepsy based on the HFO type, HFO properties, and a comparison of the phase angle of the phasor with probability density functions of phase angles derived from EEG and local field potential recordings from healthy human brain areas, healthy primate brain areas, and epileptogenic brain areas in patients with epilepsy.

A further embodiment is directed towards using a device composed of a) a subject with a plurality of electrodes; b) a brain signal acquisition device to record electrical signals from multiple locations of a subject; c) a non-transitory computer-readable memory storing instructions executable by the computer processor; d) a computer processor; e) digital outputs; f) a multichannel stimulator; g) a subject with a plurality of brain stimulating electrode(s) to utilize the report to determine when and where a brain area is engaged in memory related activity, or alternatively engaged in pathophysiological activity associated with epilepsy or epileptic seizures the device can stimulate brain region(s) with therapeutic regimens to reduce seizures, and can also stimulate brain region(s) with therapeutic regimens to enhance memory. The brain stimulation regimen is based, in part, on the detection, classification, quantification, and pathological probability of a single HFO event, and the history of a) HFO detections b) HFO classifications, c) HFO quantifications, d) derived probabilities that the HFO event's phasor is related to a physiological process or alternatively a pathophysiological process described in the report generated by the method.

A further embodiment is directed towards a method to identify, categorize, and quantify high-frequency oscillations using a topographical analysis of wavelet convolutions of electrical recordings of brain activity, identifying bursts of lower-frequency oscillations that occur during the high-frequency oscillation, and calculating a phasor based on the instantaneous phase of the burst of the slower oscillations during the HFO.

A further embodiment is directed towards a method for identifying, categorizing, and quantifying electrical signals known as high-frequency oscillations (HFO) recorded from multiple locations of a subject using an electrical sensing device and using one or more processors to: detecting electrical signals from the electrical signaling device; applying a wavelet convolution to the electrical signals to generate a first time-frequency representation of the power of the signal; determining a region of this first time-frequency plot that exceeds a threshold; wherein if the threshold is not met no HFO is registered by the apparatus; determining the topography of a second time-frequency plot temporally centered around suprathreshold region of the first time-frequency plot by identifying contours of isopower; determining at least two vertices of each contour as a coordinates of time and frequency; determining which contours exceed a specified threshold, and excluding all other contours determining each contour as open-loop or closed-loop based on the coordinates of the vertices; determining groups of contours based on their open- or closed-loop classification, power level, and time-frequency coordinates; determining an event boundary contour as the closed loop contour of lower isopower in the group that exceeds a threshold value; determining new event boundary coordinates by generating a third time-frequency plot with a lower minimum frequency limit than the second time-frequency plot and recalculating the event contours and contour group, if the minimum frequency of the original boundary contour is below a predetermined threshold; determining a duration of the HFO based on the event boundary contour; determining a mean power of the HFO by calculating a mean power magnitude across all coordinate points of the time-frequency plot within the event boundary contour; determining an amplitude-weighted mean frequency of the HFO within the event boundary contour; determining if there are open loop contours that begin and terminate at the upper frequency limit of the second time-frequency plot; determining if these open loop contours are representative of a second HFO event by calculating a fourth time-frequency plot in a higher frequency range, identifying the region of greatest power that exceeds a threshold, defining contours of isopower, determining if these are open or closed loop contours, defining groups of contours, and determining the even boundary contour; applying a distinct wavelet convolution to the electrical signals to generate a time-frequency representation of the power of the signal in a frequency range less than the HFO to determine if the HFO is superimposed on an inter-ictal discharge, or if an inter-ictal discharge has a superimposed HFO by performing a wavelet convolution to the electrical signals to generate a time-frequency representation of the power of the signal (TF Plot); determining the gradient plot of this TF plot;

$$\nabla P_f = \frac{\partial(\text{power magnitude})}{\partial(\text{time})}$$

and the vertical gradient of the TF plot $$\nabla P_f = \frac{\partial(\text{power magnitude})}{\partial(\text{frerquency})}$$

and combining these two gradients as $\nabla TF_{map} = \sqrt{(\nabla P_f)^2 + (\nabla P_t)^2}$; determining the borders of objects in the TF plot, and the gradient plot of the TF plot, discharges by binarizing the TF plot and its gradient using an appropriate threshold and applying Moore-neighbor tracing algorithm; determining the volume of the objects in the TF plot, and the gradient plot of the TF plot, using trapezoidal surface integration within the object borders derived from the binarized TF plot to the unbinarized TF plot, and gradient plot of the TF plot; determining if any of the objects are near the borders of the TF plot, or have a height-width ratio less than a threshold and excluding these object from further analysis; determining if an object is representative of an inter-ictal discharge by defining the object of greatest volume in the TF plot, and object of greatest volume in the gradient plot of the TF plot, and calculating if the volume of these objects exceeds pre-defined thresholds; filtering the electrical signals recorded from multiple locations of a subject using an electrical sensing device to produce a low-frequency data stream to determine if the preferred phase angle of coupling between the HFO and bursts of slower oscillations; transforming the low-frequency data stream to produce a low-frequency instantaneous phase; and instantaneous amplitude; determining the start and end times of an oscillatory burst by smoothing the instantaneous amplitude function and applying predetermined thresholds; determining if the HFO coincides with one or several oscillatory burst epochs; determining a HFO phasor with a mean phase angle and vector strength value based on the low-frequency burst instantaneous phase and the mean HFO event power magnitude across the boundary counter; determining an HFO duration, an HFO mean power, an HFO mean frequency, and HFO phasors for all HFO events defined in the electrical signals from multiple locations; identifying a location of the brain corresponding with the same electrical signals determined to displays HFOs of a predefined HFO duration, HFO mean power, HFO mean frequency, and HFO phasors based on where the electrical signals were recorded; and generating a report of the identified location of the subject as a target for a therapeutic procedure for treating a cause of the identified HFO.

A further preferred embodiment is directed towards a system for identifying brain electrical activity displaying high-frequency oscillations, comprising: a data acquisition device for receiving an electrical signal sensing device configured to record electrical signals from multiple locations of the patient; a memory storage system for storing instructions; and a microprocessor communicatively coupled to the memory storage system, the microprocessor being configured to execute instructions stored in the memory storage system to cause the system to: record, using the electrical signal sensing device, electrical signals from multiple locations in the brain of a subject; filter the electrical signals to produce a high frequency oscillation (HFO) data stream and a low-frequency data stream; apply independent component analysis to the HFO data stream and removing noise from the HFO data stream; determine the location of HFO events in the HFO data stream; apply a wavelet convolution to the electrical signals at the location of HFO events to generate a time-frequency plot representation of the power of the signal; determine a region of the first time-frequency plot that exceeds a threshold; wherein if the threshold is not met no HFO is registered by the apparatus; determine the topography of a second time-frequency plot temporally centered around suprathreshold region of the first time-frequency plot by identifying contours of isopower; determine at least two vertices of each contour as a coordinates of time and frequency; determine which contours exceed a specified threshold, and excluding all other contours; determine each contour as open-loop or closed-loop based on the coordinates of the vertices; determine groups of contours based on their open- or closed-loop classification, power level, and time-frequency coordinates; determine an event boundary contour as the closed loop contour of lower isopower in the group that exceeds a threshold value; determine new event boundary coordinates by generating a third time-frequency plot with a lower minimum frequency limit than the second time-frequency plot and recalculating the event contours and contour group, if the minimum frequency of the original boundary contour is below a predetermined threshold; determine a duration of the HFO event based on the event boundary contour; determine a mean power of the HFO by calculating the mean power magnitude across all coordinate points of the time-frequency plot within the event boundary contour; determining an amplitude-weighted mean frequency of the HFO even within the boundary contour; determine if there are open loop contours that begin and terminate at the upper frequency limit of the second time-frequency plot; determine if these open loop contours are representative of a second HFO event by calculating a fourth time-frequency plot in a higher frequency range, identifying the region of greatest power that exceeds a threshold, defining contours of isopower, determining if these are open or closed loop contours, defining groups of contours, and determining the even boundary contour; applying a distinct wavelet convolution to the electrical signals to generate a time-frequency representation of the power of the signal in a frequency range less than the HFO to determine if the HFO event is superimposed on an inter-ictal discharge, or if an inter-ictal discharge has a superimposed HFO by performing a wavelet convolution to the electrical signals to generate a time-frequency representation of the power of the signal (TF plot); determine the gradient plot of this TF plot; by calculating both the horizontal gradient of the TF plot;

$$\nabla P_t = \frac{\partial(\text{power magnitude})}{\partial(\text{time})};$$

and the vertical gradient of the TF plot, $$\nabla P_f = \frac{\partial(\text{power magnitude})}{\partial(\text{frerquency})};$$

and combining these two gradients as $\nabla T\ F_{map} = \sqrt{(\nabla P_f)^2 + (\nabla P_t)^2}$; determining the borders of objects in the TF plot, and the gradient plot of the TF plot, discharges by binarizing the TF plot and its gradient using an appropriate threshold and applying Moore-neighbor tracing algorithm; determine the volume of the objects in the TF plot, and the gradient plot of the TF plot, using trapezoidal surface integration within the object borders derived from the binarized TF plot to the unbinarized TF plot, and gradient plot of the TF plot; determine if any of the objects are near the borders of the TF plot, or have a height-width ratio less than a threshold and excluding these object from further analysis; determine if an object is representative of an inter-ictal discharge by defining the object of greatest volume in the TF plot, and object of greatest volume in the gradient plot of the TF plot, and calculate if the volume of these objects exceeds pre-defined thresholds; filter the electrical signals recorded from multiple locations of a subject using an electrical sensing device to produce a low-frequency data stream to determine if the preferred phase angle of coupling between the HFO and bursts of slower oscillations; transform the low-frequency data stream to produce a low-frequency instantaneous phase; and instantaneous amplitude; determine the start and end times of oscillatory bursts by smoothing the instantaneous amplitude function and applying predetermined thresholds; determine if the HFO coincides with one or several oscillatory burst epochs; determine a HFO phasor with a mean phase angle and vector strength value based on the low-frequency burst instantaneous phase and the mean HFO event power magnitude across the boundary counter; determine the probability that a HFO resulted from either a process involved with memory and cognition, or a pathophysiological process involved with epilepsy on the basis of a comparison of the HFO duration, HFO mean power, HFO mean frequency, and HFO phasor with a pre-existing database of the values of these parameters; identify a location of the brain corresponding with the same electrical signals determined to displays HFOs of a pre-defined HFO duration, HFO mean power, HFO mean frequency, HFO phasors, and pathological HFO probability, based on where the electrical signals were recorded; and generate a report of the identified location of the subject as a target for a therapeutic procedure for treating a cause of the identified HFO events.

A further embodiment is directed towards non-transitory computer readable medium storing instructions that, when executed by a processor, are configured to identify brain electrical activity displaying of a predefined HFO duration, HFO mean power, HFO mean frequency, and HFO phasor were recorded by: receiving electrical signals recorded from multiple locations in the brain of a subject using an electrical signal sensing device; filtering the electrical signals to produce a high frequency oscillation (HFO) data stream and a low-frequency data stream; applying independent component analysis to the HFO data stream and removing noise from the HFO data stream; determining the location of HFO events in the HFO data stream; applying a wavelet convolution to the electrical signals at the location of HFO events to generate a time-frequency representation of the power of the signal; determining a region of this first time-frequency plot that exceeds a threshold; wherein if the threshold is not met no HFO is registered by the apparatus; determining the topography of a second time-frequency plot temporally centered around suprathreshold region of the first time-frequency plot by identifying contours of isopower; determining at least two vertices of each contour as a coordinates of time and frequency; determining which contours exceed a specified threshold, and excluding all other contours; determining each contour as open-loop or closed-loop based on the coordinates of the vertices; determining groups of contours based on their open- or closed-loop classification, power level, and time-frequency coordinates; determining an event boundary contour as the closed loop contour of lower isopower in the group that exceeds a threshold value; determining new event boundary coordinates by generating a third time-frequency plot with a lower minimum frequency limit than the second time-frequency plot and recalculating the event contours and contour group, if the minimum frequency of the original boundary contour is below a predetermined threshold; determining a duration of the HFO event based on the event boundary contour; determining a mean power of the HFO by calculating the mean power magnitude across all coordinate points of the time-frequency plot within the event boundary contour; determining an amplitude-weighted mean frequency of the HFO even within the boundary contour; determining if there are open loop contours that begin and terminate at the upper frequency limit of the second time-frequency plot; determining if these open loop contours are representative of a second HFO event by calculating a fourth time-frequency plot in a higher frequency range, identifying the region of greatest power that exceeds a threshold, defining contours of isopower, determining if these are open or closed loop contours, defining groups of contours, and determining the even boundary contour; applying a distinct wavelet convolution to the electrical signals to generate a time-frequency representation of the power of the signal in a frequency range less than the HFO to determine if the HFO event is superimposed on an inter-ictal discharge, or if an inter-ictal discharge has a superimposed HFO by performing a wavelet convolution to the electrical signals to generate a time-frequency representation of the power of the signal (TF plot); determining the gradient plot of this TF plot; by calculating both the horizontal gradient of the TF plot;

$$\nabla P_t = \frac{\partial (\text{power magnitude})}{\partial (\text{time})};$$

and the vertical gradient of the TF plot, $$\nabla P_f = \frac{\partial (\text{power magnitude})}{\partial (\text{frerquency})};$$

and combining these two gradients as, $\nabla TF_{map} = \sqrt{(\nabla P_f)^2 + (\nabla P_t)^2}$; determining the borders of objects in the TF plot, and the gradient plot of the TF plot, discharges by binarizing the TF plot and its gradient using an appropriate threshold and applying Moore-neighbor tracing algorithm; determining the volume of the objects in the TF plot, and the gradient plot of the TF plot, using trapezoidal surface integration within the object borders derived from the binarized TF plot to the unbinarized TF plot, and gradient plot of the TF plot; determining if any of the objects are near the borders of the TF plot, or have a height-width ratio less than a threshold and excluding these object from further analysis; determining if an object is representative of an inter-ictal discharge by defining the object of greatest volume in the TF plot, and object of greatest volume in the gradient plot of the TF plot, and calculating if the volume of these objects exceeds pre-defined thresholds; filtering the electrical signals recorded from multiple locations of a subject using an electrical sensing device to produce a low-frequency data stream to determine if the preferred phase angle of coupling between the HFO and bursts of slower oscillations; transforming the low-frequency data stream to produce a low-frequency instantaneous phase; and instantaneous amplitude; determining the start and end times of oscillatory bursts by smoothing the instantaneous amplitude function and applying predetermined thresholds; determining if the HFO coincides with one or several oscillatory burst epochs; determining a HFO phasor with a mean phase angle and vector strength value based on the low-frequency burst instantaneous phase and the mean HFO event power magnitude across the boundary counter; determining the probability that a HFO resulted from either a process involved with memory and cognition, or a pathophysiological process involved with epilepsy on the basis of a comparison of the HFO duration, HFO mean power, HFO mean frequency, and HFO phasor with a pre-existing database of the values of these parameters; identifying a location of the brain corresponding with the same electrical signals determined to displays HFOs of a predefined HFO duration, HFO mean power, HFO mean frequency, HFO phasors, and pathological HFO probability, based on where the electrical signals were recorded; and generating a report of the identified location of the subject as a target for a therapeutic procedure for treating a cause of the identified HFO events.

DETAILED DESCRIPTION OF THE EMBODIMENTS

Figure 1:
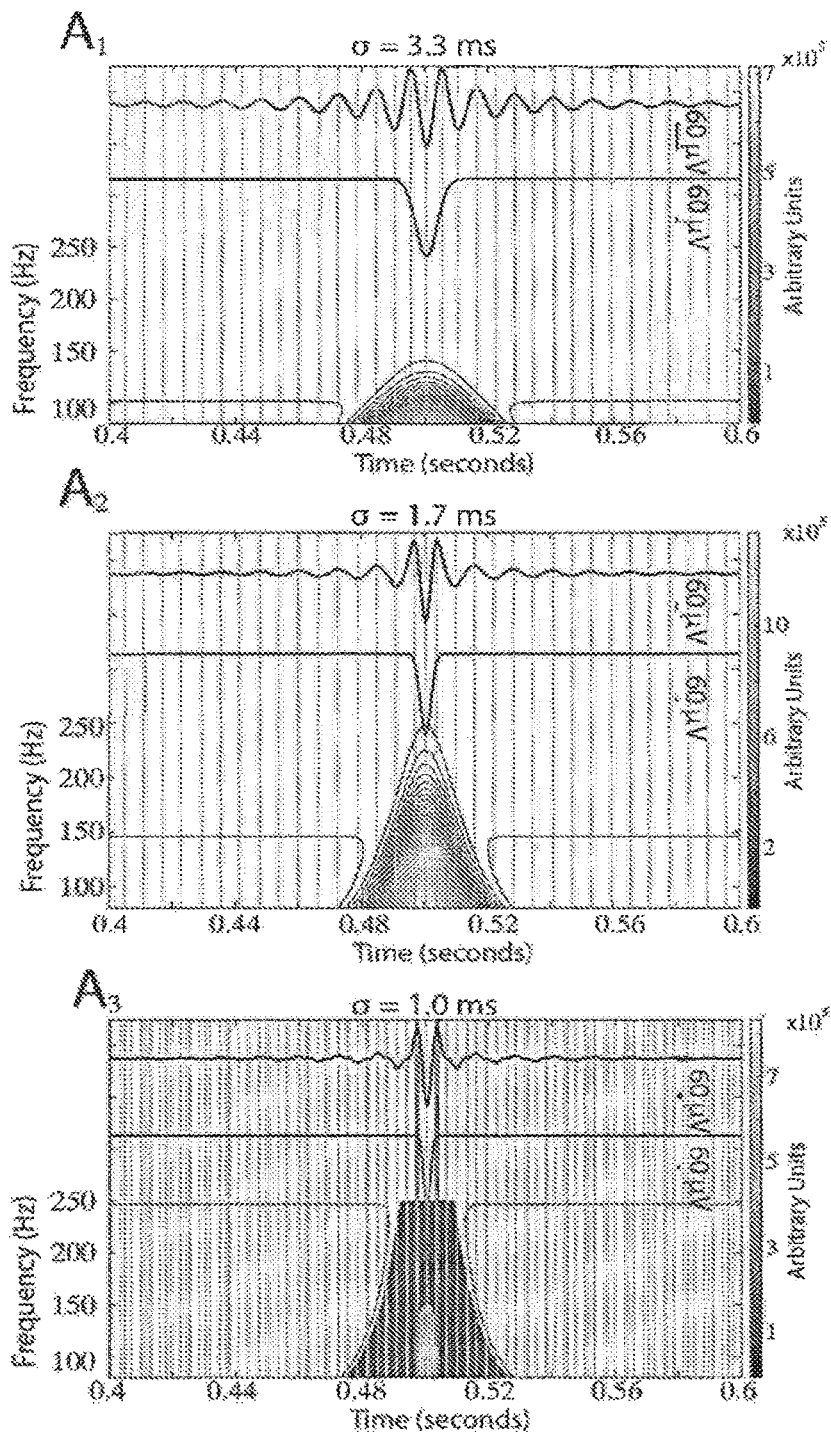
FIG. 1 depicts simulations showing proof of concept of topographical analysis of time-frequency plots used by the method.
Figure 1:
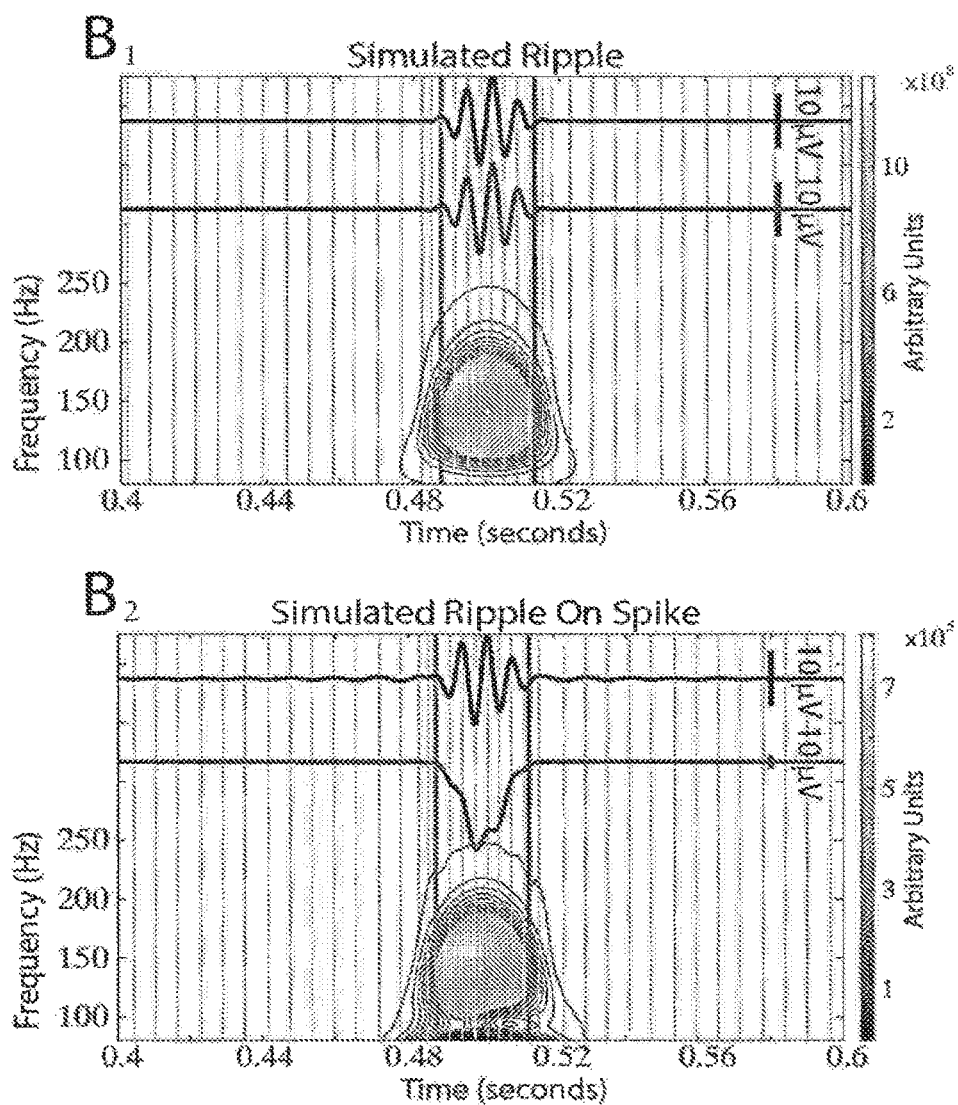

In both manual and automated HFO detection, it is common practice to first apply a high pass filter to the continuous intracranial EEG (iEEG) or local field potential (LFP) recordings. After high-pass filtering, HFOs can be observed visually or detected automatically as an increase in the signal amplitude above a threshold of 3-5 standard deviations of the mean for at least three oscillatory cycles.

However, when sharp transients such as inter-ictal epileptiform spikes (IES) are band-pass filtered a sinusoid-like waveform resembling an HFO can result. The energy spread over a continuous broad frequency range is due to how transients are represented in the frequency space, because the Fourier transform of a Dirac impulse is a constant.

One strategy for distinguishing true HFOs from false HFOs is based on time-frequency analysis using wavelets. A wavelet convolution or transform of a sharp transient appears as a "candle" with a gradual and continuous taper in power with increasing frequency, while a true oscillation appears as a distinct "blob" of power in time-frequency coordinates.

We utilized the difference in the time-frequency representation of sharp transients and true high-frequency oscillations, to develop an automatic software method for classifying and quantifying ripples. Time-frequency maps of time series have an inherent topography defined by isopower contours. A true ripple is represented by a "blob" of power within the ripple band (80-250 Hz) and if contour lines are defined for a time-frequency representation of the "blob", with the maximum and minimum frequencies constrained to the ripple band, the contours will have closed loops. In contrast, a false ripple is represented by a "candle" of power in the ripple band, but importantly this "candle" extends below the ripple band. Therefore, when the contour lines are defined for the "candle" within the ripple band, the contours will have open loops. In the current study we tested whether the open-, or closed-loop properties of time-frequency plot contour lines could be used to differentiate true- and false-ripples on spikes i.e. epileptiform discharges, and whether analysis of the contour lines could be used to define ripple spectral content, power, and duration.

Patients: Recordings were selected from patients who underwent intracranial monitoring with depth electrodes between 2014 and 2016 at University of California Los Angeles (UCLA) and 2016-2017 at Thomas Jefferson University (TJU) for the purpose of localization of the seizure onset zone. The inclusion criteria were at least one night and day of intracranial recording with 2000 Hz sampling rate and at least 4 h of v EEG uninterrupted by seizures. All clinical data from the patient's inpatient and postsurgical follow-up charts were provided. Patients underwent pre-surgical magnetic resonance imaging (MRI) and stereotactic electrode implantation, as well as a CT scan to localize electrode and a postsurgical MRI after the respective surgery. This study was approved by the UCLA institutional review board, and TJU institutional review board.

EEG Recordings and segment selection: Clinical iEEG (0.1-600 Hz; 2,000 samples per second; reference scalp Fz) was recorded from 7-contact depth electrodes using a Nihon-Kohden 256-channel JE-120 long-term monitoring system (Nihon-Kohden America, Foothill Ranch, CA, U.S.A.). The recordings were acquired during a 35-60 min epoch of mixed-stage sleep. Sleep was confirmed by video-EEG inspection revealing K-complexes, spindles, slow waves, and a paucity of muscle artifact. We did not perform concurrent electrooculography (EOG) and electromyography (EMG) recordings. One-second trials of ripples occurring on inter-ictal discharges were identified using a previously described algorithm. In brief, 1) INFOMAX independent component analysis was applied to referential recordings to reduce muscle contamination, and demarcate artefactual ripple events produced by muscle contamination (US20150099962A1) (WO2017143319A1) 2) ripples were detected using a Hilbert detector applied to the band-pass filtered and ICA processed signal, 3) for each ripple detected a one-second trial was generated with a ripple centered at 0.5 seconds, 4) To distinguish ripples that occur during epileptiform spikes from all other ripples, we utilized a validated method. We calculated the derivative of the peri-ripple band-pass filtered (4-30 Hz) iEEG and applied a threshold of 4 µV/msec. If the one second iEEG trials containing ripple events exceeded this threshold within +/−50 msec that ripple was included for subsequent analysis. All the analysis in this study was performed using custom software written in Matlab 2016b (Natick, MA).

Upon collection of data, we can then process the data in a new and meaningful way. Furthermore, by identifying true events, we can treat the patient with electrical stimulation to increase memory or engage memory or to impact the brain to reduce or eliminate seizure activity or other activity having deleterious effects on the brain.

Wavelet Convolution: A time-frequency analysis of the iEEG recording was performed using a wavelet convolution in the time domain. Complex Morlet wavelets were created with constant frequency domain width $$\frac{f_o}{\sigma_f} = 7,$$

where $f_o$ is the wavelet central frequency and $\sigma_f$ is the standard deviation of its Gaussian envelope in the frequency domain. The central frequency, and the standard deviation of the Gaussian envelope values were frequency dependent and varied between the lower and upper limits of the TF analysis. The Gaussian width of the wavelet was set to 5 standard deviations. Prior to performing the wavelet convolution, the digital recording of the brain signal was padded with zeros until the sample count was equal to the closest power of two greater than the initial number of samples. The time frequency plot was not normalized. Ripple events occur within a range of 80-200 Hz. Due to boundary effects caused by continuous wavelet convolution of finite-length signals, a range of 50-240 Hz was selected for the time-frequency (TF) plot in order to buffer the frequency range of interest. We also discarded the initial and final 45 msec of the time-frequency (TF) plot to reduce boundary effects.

Topographical analysis of the time-frequency plot: The topographical analysis of the TF plot was performed by calculating a contour map consisting of 50 contours of isopower in the region of the TF plot centered on the candidate event, determined by the Hilbert detector, and including 100 milliseconds prior to the event, and 100 milliseconds after the event. Over the total range of power values in the TF plot, 50 contour levels were computed and scaled as equal data unit lengths. Contours corresponding to power values less than a threshold defined by 0.2*((max$_{tf\text{-}power}$−min$_{tf\text{-}power}$)+min$_{tf\text{-}power}$) were removed. The method next identified all the vertices of each of the remaining isolines of constant power in the TF map. Thus each contour was described by its power magnitude level, and the time/frequency coordinates of its vertices.

Defining groups of open- and closed-loop contours A power threshold was then applied to each of the 50 isolines of constant power in the TF plot of the candidate event, and contours below a power threshold were removed. Each of the remaining contours was subsequently classified as closed if the contour's first and last vertex coordinate was identical, and open if the first and last vertex were distinct. Groups of closed-loop contours, which either surround or are surrounded by other closed-loop contours, were identified. If, in a group, the contour with the highest power level surrounded the other members of that group, the group was identified as a valley and removed from the time-frequency map. Groups containing fewer than 3 closed-loop contours were categorized as a 'lone contour group' and were removed from consideration. If one or more closed-loop contour groups remained, the candidate true ripple on spike event is identified as the group associated with the highest local maximum. In this study, all 1-second iEEG trials that were analyzed using the topographical approach were believed to contain either a ripple oscillation, and/or inter-ictal epileptiform discharge. In the case that neither of these events were present in the trial, then the detector would still define.

Quantifying ripple on spike duration, power, and spectral content: In contrast to HFO detectors that band-pass filter the recordings (US20150099962A1, US20170311870A1, US20160045127A1), or also apply a wavelet transforms (U.S. Pat. No. 9,326,698B2) and use amplitude and/or power based criteria to identify HFO events, the method described herein identified distinct objects in the time-frequency plot to using a topographical analysis to identify, classify and quantify HFO events. Only closed-loop contours that surround event maximum and are greater than the detection threshold were considered for property extraction. The contour at the lowest power level was selected as the event boundary contour 'B'. The region of the TF map within this boundary was defined as the ripple event, from which the relevant properties were be extracted. Four properties were extracted from the event region. The first two were the times of event onset and offset for determination of the event duration. These onset and offset times were defined as the minimum and maximum time coordinates associated with the vertices of the boundary contour. The power of the HFO was then determined by calculating the mean power across all coordinate points of the TF map within the boundary B. Finally, the amplitude-weighted mean frequency of the HFO event was calculated using:

$$\overline{f_{hfo}} = \sum_i^B \frac{f_i * P_i}{\Sigma P_i} \qquad \text{eqn. 1}$$

Wherein $f_i$ and $P_i$ and are the frequency and power amplitude of coordinate of the TF map within the boundary contour, B.

Illustrating detector methodology using simulated data: We used Gaussian functions of varying duration to simulate inter-ictal epileptiform spikes in computer generated 1 second data segments with a 2 kHz sampling rate. The Gaussians were generated using the function gausswin.m with σ=2, 3.3, 6.7. We generated simulated ripples using a sine wave function with a frequency of 140 Hz and an amplitude of 350 to correspond with the respective amplitude of the Gaussian function. A Blackman window was applied to the sine wave for the purpose of amplitude modulation. A simulated ripple on epileptiform spike was created by combining the Gaussian function (σ=6.7) with the simulated ripple.

Quantifying detector performance using simulated data: A 1-second 2 kHz sampled iEEG trial was selected from one patient to calculate surrogate trials for the simulation study. This trial was selected on the basis of the absence of a ripple or inter-ictal epileptiform spike. We computed the fast fourier transform of this iEEG trial (fft.m) for all frequencies less than the Nyquist frequency in 1 Hz bins. The imaginary components of the FFT were permuted using randperm.m. A iEEG surrogate trials was derived from the original iEEG trial using an inverse fast fourier transform (ifft.m) of the real and permuted imaginary components of the original iEEG trial. A simulated ripple with a frequency of 100 Hz and a duration of 0.0268 seconds was generated using a sine function enveloped by a Gaussian window of the form $$e - \frac{1}{2}\left(\frac{2\alpha\left(n+\frac{N}{2}+1\right)}{N-1}\right)^2$$

with α=75. The amplitude of the sine function ranged from 2-30 μV in 2 μV steps to simulate varying ripple intensities. The simulated ripple was superimposed at 0.5 seconds on the 1000 permuted iEEG trials.

Validation of detector accuracy by visual inspection: The classification of ripple on spike events as true or false was validated using visual inspection of a custom display of the raw and processed data. In a single window each trial was displayed as 1) the unfiltered one second iEEG recording trial, 2) the iEEG trial following band-pass (80-240 Hz) filtering using a $500^{th}$ order digital FIR filter, 3) vertical guidelines located at the peaks, and troughs (blue) of the band-pass filtered signal superimposed on the unfiltered and filtered iEEG trial, 4) the TF plot, 5) the isopower contour lines resulting from the topographical analysis, 6) the candidate closed-loop contour group, or open-loop contour group.

Defining true and false high-frequency oscillations: To test the accuracy of the detector to discriminate true from false ripples on spikes (RonS), we manually separated true and false RonS using the following criteria. A true RonS corresponded with a visible ripple superimposed on the spike in the unfiltered iEEG, and the peaks and troughs of the ripple component of the RonS were largely aligned with the peaks and troughs respectively of the RonS after band-pass (80-240 Hz) filtering. In contrast, a false RonS was not visible evidence of ripple on the spike or when present had no temporal alignment between the peaks and troughs of the unfiltered and the band-pass filtered signal.

Identification of superimposed inter-ictal discharges in the iEEG using a topographical analysis of time-frequency plots: Both true and false ripple events were subsequently processed by a second stage algorithm designed to identify the presence of an inter-ictal discharge, within 200 ms of the ripple event, on the basis of an analysis of TF plots resulting from wavelet convolution. This algorithm operated under the principle that inter-ictal discharges produce a recognizable motif in TF plot that is relatively independent of both the amplitude and slope of the iEEG during the discharge. The novel detector sought to identify this motif by using a topographical analysis of the TF plot that identified and characterized distinct elevations in both the power, and the gradient of the power, in TF space. These elevations represent objects and we hypothesized that objects that met certain criteria would always correspond with inter-ictal epileptiform spike events. We identified these candidate events by first creating objects by thresholding the TF plot and its gradient to values >20% of the maximum. After applying this threshold it was possible to define the borders of the objects in the resulting TF plot, and its gradient, by using this same threshold to derive a binary map. We subsequently calculated the volume of each object, within its defined boundaries, using a trapezoidal surface integration for each of the objects. To determine if any of the identified and characterized objects were representative of inter-ictal epileptiform spikes we applied separate thresholds to the derived volumes for the objects in the TF plot and its gradient. Specifically, the iEEG trials were processed using a real Morlet-based wavelet convolution to compute the TF map.

The wavelets were created with constant frequency domain width, $$\frac{fo}{\sigma f} = 6$$

We analyzed the portion of the resulting TF plot centered around the detected ripple event±200 ms. We derived a gradient plot of the TF plot by calculating both the horizontal gradient of the TF plot, $$\nabla Pt = \frac{\partial(\text{power magnitude})}{\partial(\text{time})};$$

and the vertical gradient of the TF plot, $$\nabla Pf = \frac{\partial(\text{power magnitude})}{\partial(\text{frequency})},$$

and combining these two gradients as, $$\nabla TF_{map} = \sqrt{(\nabla P_f)^2 + (\nabla P_t)^2}.$$

To define the thresholds for both the TF plot and its gradient used to define the object boundaries we used 20% of the respective maximum values. Following binarization of the maps using this threshold we identified the boundary coordinates of each object using a Moore-neighbor tracing algorithm modified by Jacob's stopping criteria. We then determined the volume of each object within its boundaries by approximating the surface integral using trapezoidal numerical integration.

To identify the objects that corresponded to inter-ictal epileptiform spikes, we first identified the object with the greatest power maximum value. We then determined if the volume of this object met a predetermined threshold and if in the gradient plot corresponding objects also met a predetermined threshold. The correspondence of the object in the time-frequency plot and the objects in the gradient plot was confirmed by measuring the distance between the centroids of these objects. Due to edge effect we excluded objects in the TF plot that had a power maximum value near the TF plot borders. We also excluded objects that had a height-width ratio less than 0.7, because these objects more often represented bursts of gamma oscillations.

Figure 2A:
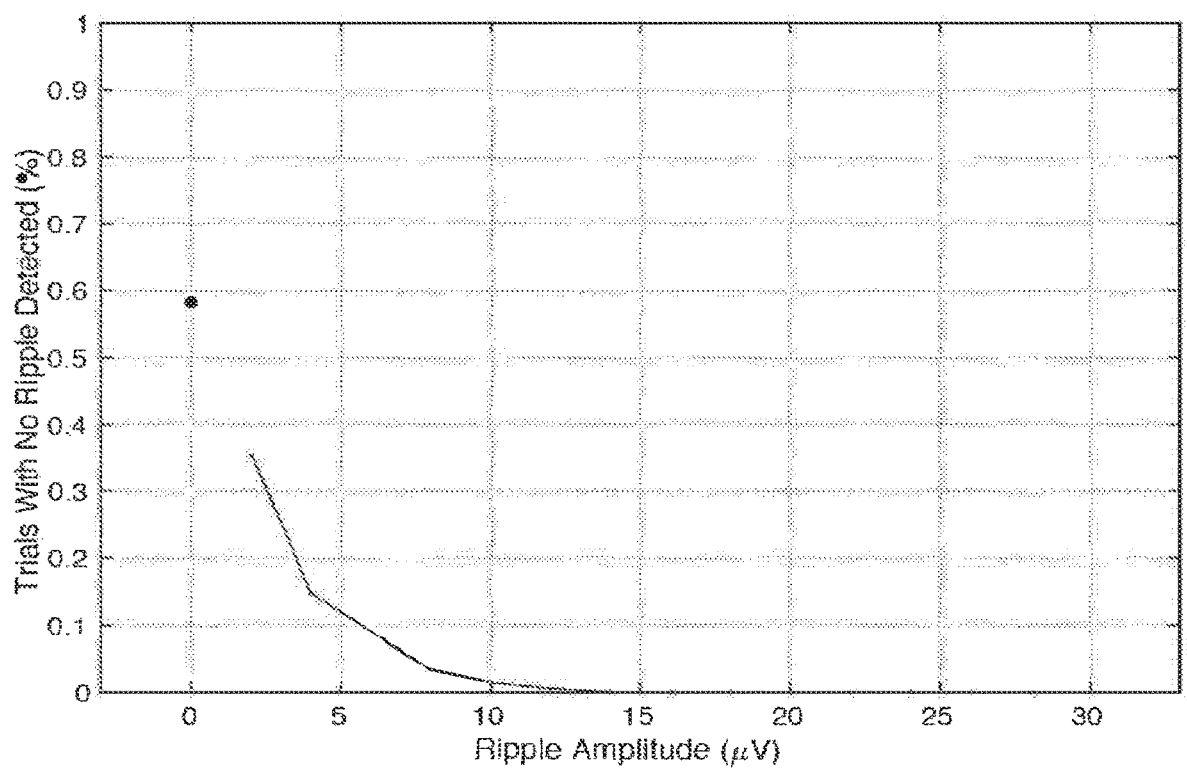
FIGS. 2A-2D depict results of simulations of the topographical detection and quantification of HFOs in EEG used by the method.
Figure 2B:
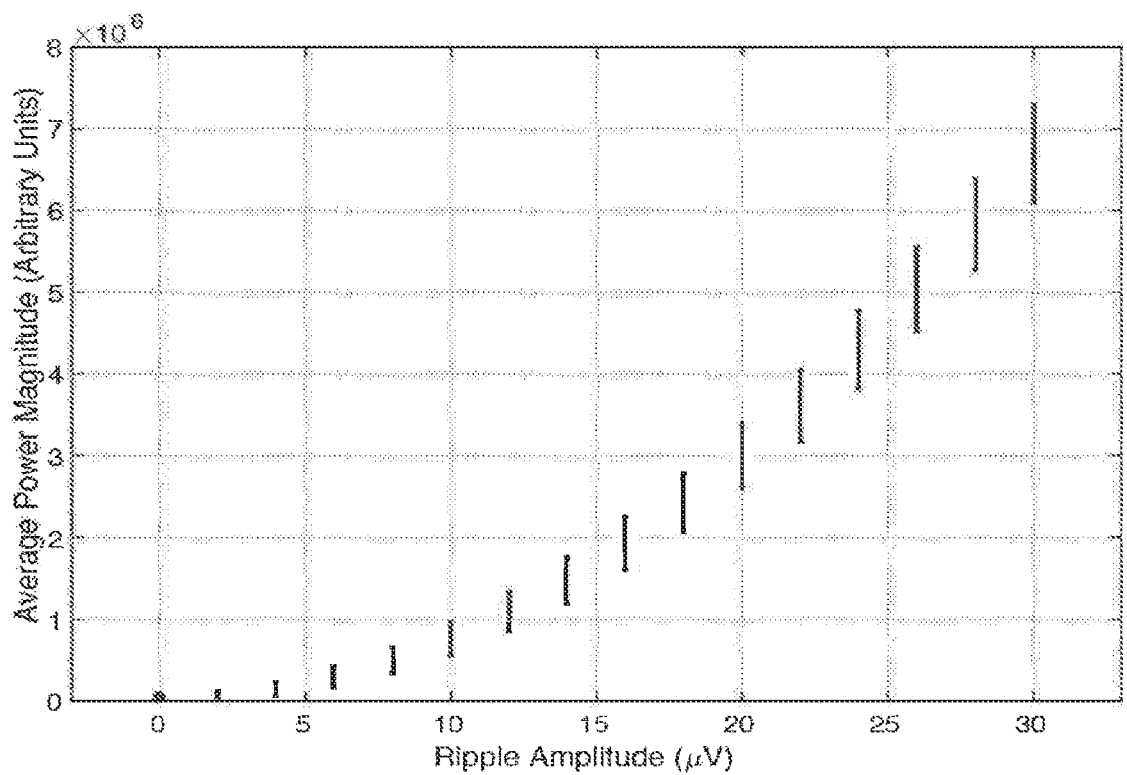
Figure 2C:
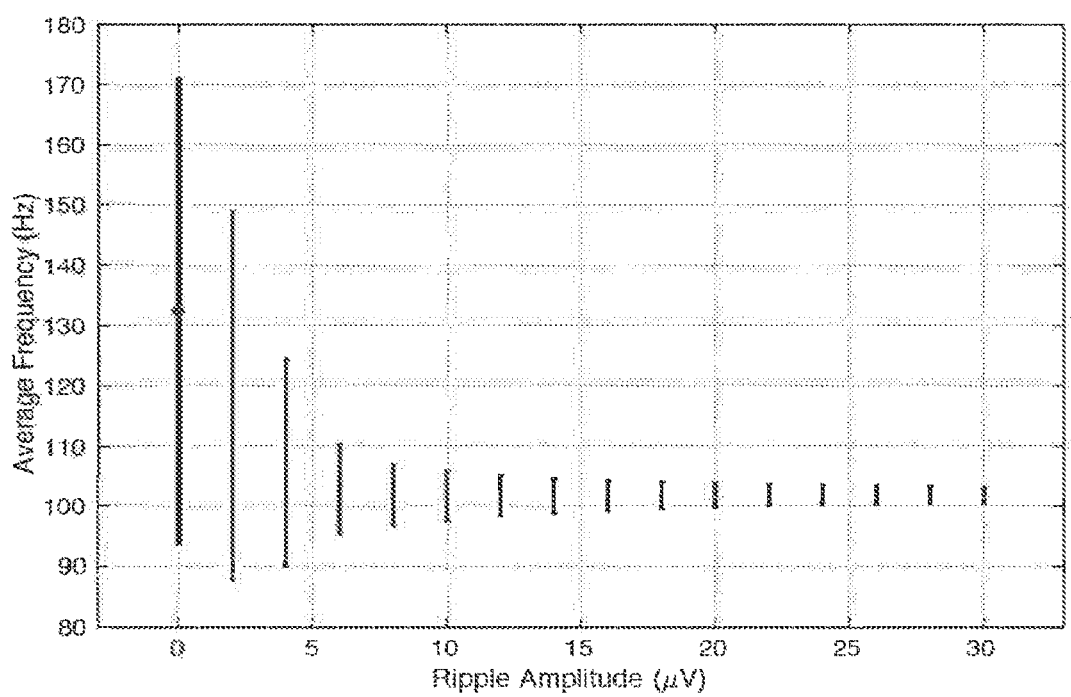
Figure 2D:
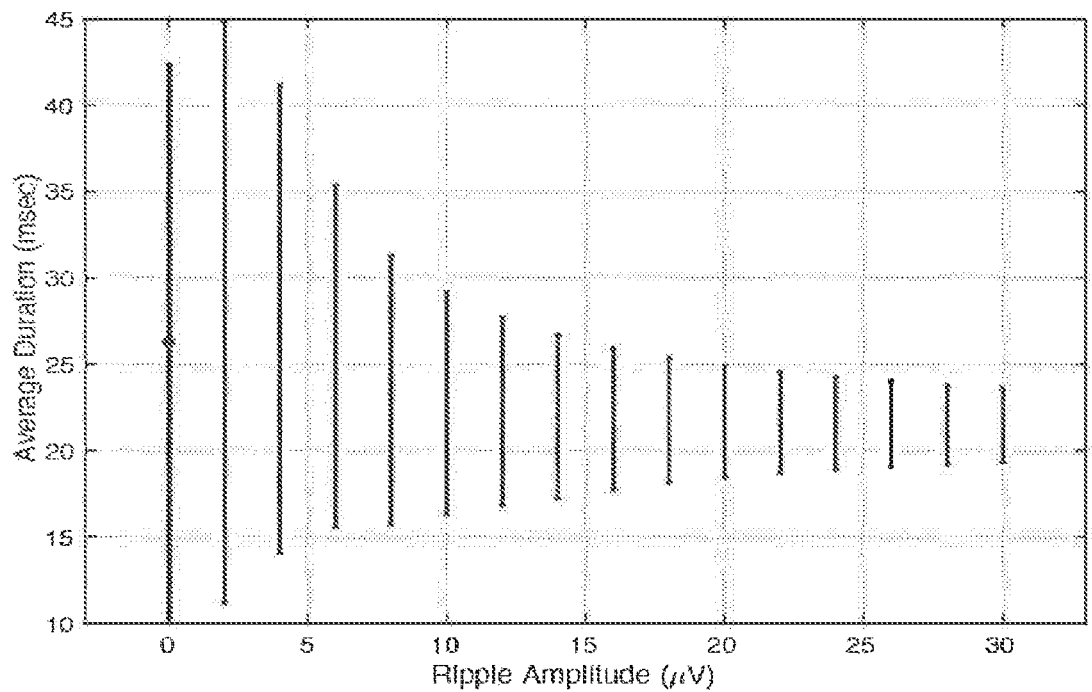
Figure 3:
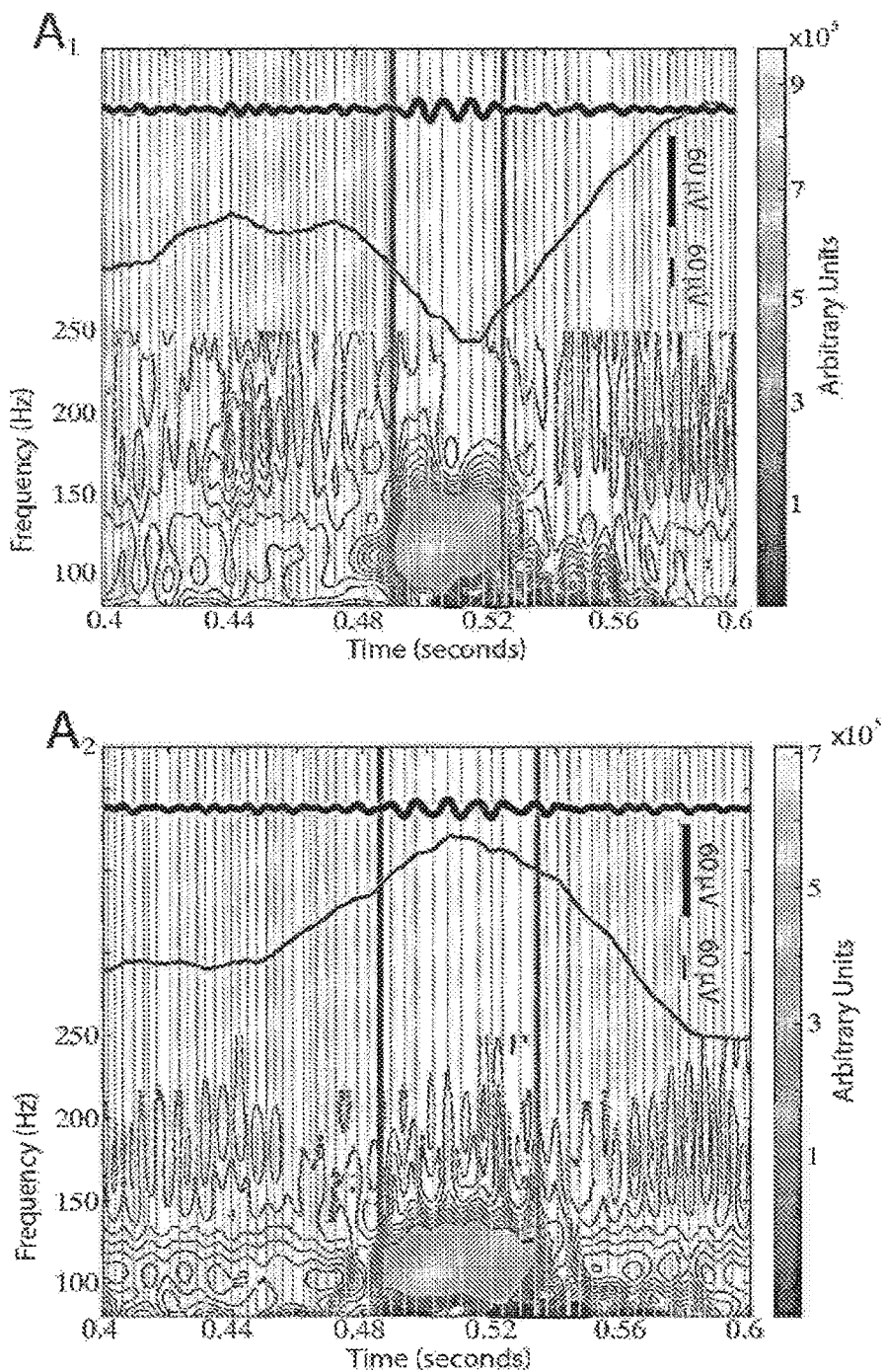
FIG. 3 depicts results of the topographical detection and quantification of HFOs in human EEG recordings by the method.
Figure 3:
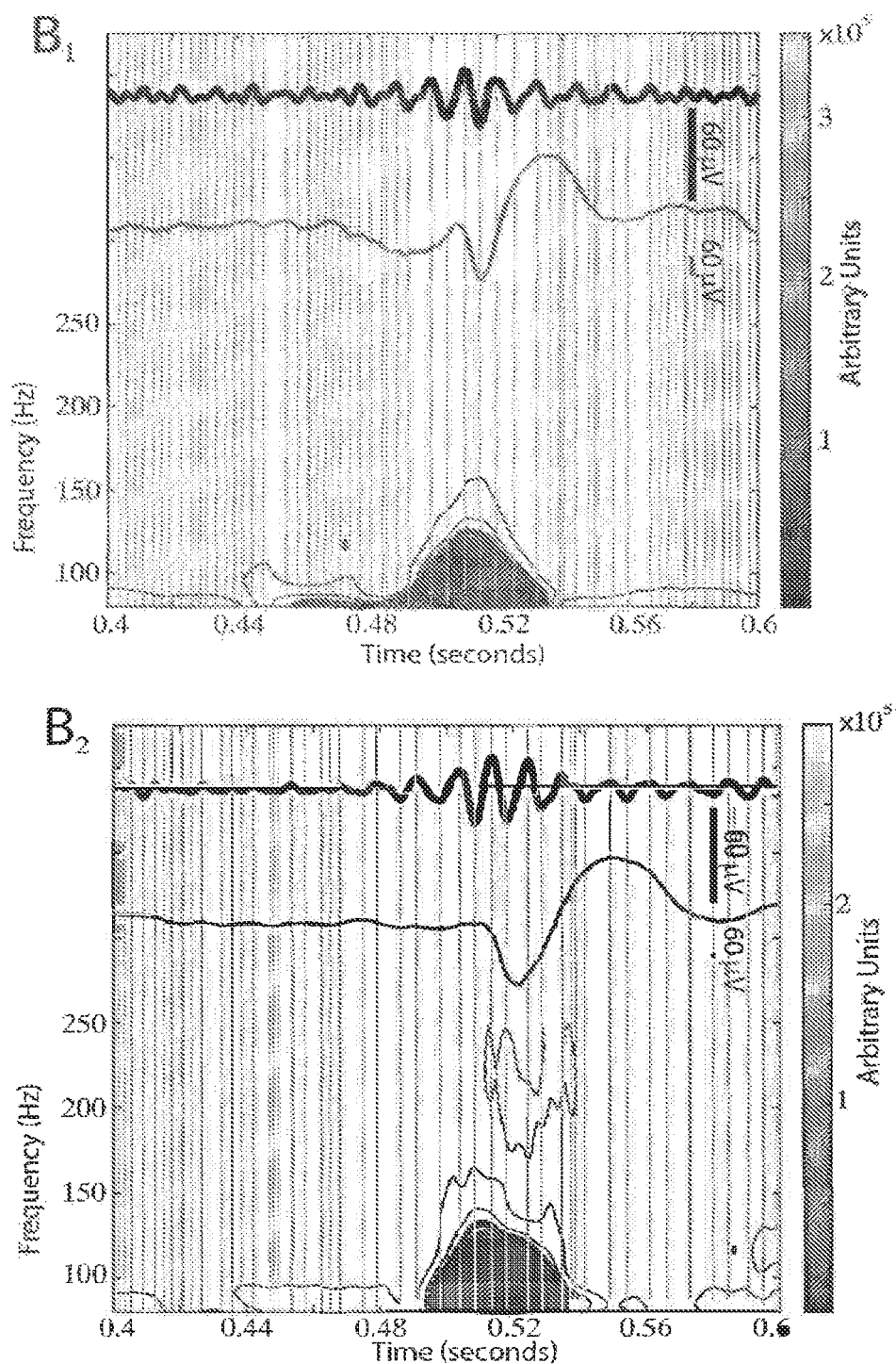

Illustration of detector principles: On the basis of these operational definitions, and assumptions we applied the detector to simulated data to illustrate how a topographical analysis of time frequency spectrograms could differentiate true and false ripples on spikes. The time frequency plots of Gaussians with durations of σ~1.0 ms were described by a set of open-loop contours of isopower (CLCs) extending up from the lower frequency limit (80 Hz), reaching a peak frequency inversely proportional to the duration of the Gaussian signal (FIG. 1A1, 2). When the duration of the Gaussian was decreased to σ−1.0 ms, a group of closed-loop contours of isopower (CLCs) were evident (FIG. 1A3). Since no true ripple oscillation was present during the Gaussians, the peaks and troughs of the band-pass filtered simulated signals showed incomplete correspondence with the raw simulated signal (FIG. 1A1-3). A simulated ripple event resulted in a CLC group of isopower centered at the simulated ripple's mean frequency (FIG. 1B1, light region). In this case, the peaks and troughs of the band-pass filtered signal did coincide with the raw simulated signal (FIG. 1B1, top black and light waveform). When the simulated ripple event was combined with a Gaussian the detector registered a set of CLCs extending from the lower frequency limit and a CLCs group centered at the ripple's mean frequency (FIG. 1B2, light), and the peaks and troughs of the raw signal corresponded with the peaks and troughs of the band-pass filtered signal (FIG. 1B2, top black and light waveform).

Measuring detector performance using simulated data: Using simulated iEEG data, we sought to determine the stability and variability of ripple identification and characterization. Ripples of a predetermined magnitude, identical in duration and spectral content, were superimposed on simulated iEEG trials generated by randomly permuting the phase component of patient's 1 second a featureless iEEG recording. Since the topographical algorithm is designed to always identify a closed or open loop contour group true or false ripple event, regardless of whether either is actually present the power of the group, we first asked what fraction of the simulated iEEG trials, lacking a superimposed simulated ripple, would result in a closed loop contour. Thus, the algorithm was first used to process simulated trials with no superimposed ripple in order to asses in what ways background iEEG may trigger false positive detections and to examine the behavior of the calculated features. We found that when no ripple was present in the simulated data, the detector identified closed loop groups in 41.5% of background iEEG trials with no superimposed ripple oscillation resulted in a CLC group, triggering a false positive detection the trials (FIG. 2A). The mean average power magnitude detected for these false positive events corresponded to ripple amplitudes<5 uV (FIG. 2B). (max average power less than mean average power for ripples with 5 uV amplitudes). We next introduced the superimposed ripple to the simulated iEEG background. We found that the probability of false negative ripple identification decreased exponentially with increasing simulated ripple amplitude. As the simulated ripple amplitude was increased, the average power weighted mean frequency estimated by the detector approached a frequency of 101.6 Hz, slightly above the simulated frequency of the simulated ripple of 100 Hz. The standard deviation of the average frequency of the detected ripple decreased exponentially (FIG. 2C). Increasing the amplitude of the simulated ripple corresponded with an increase in the power of the identified ripple, as well as an increase in the standard deviation of this measurement (FIG. 2B). Finally, the increasing amplitude also corresponded with a decrease in the variability of the detected ripple duration. The simulated ripple duration was consistently underestimated by the topographical method (FIG. 2D).

iEEG Visual Verification and Detector Performance: The detector was applied to 25,011 one-second iEEG trials, recorded from 12 patients undergoing intracranial monitoring with depth electrodes that recorded RonS events. In all these trials the detector could differentiate the true RonS trials from the false RonS trials, and characterize the properties of the former. False RonS have no mean spectral content, or centroid of power since they result from Gibb's phenomenon. We randomly selected 2,934 trials for visual verification. A true positive was defined as a trial in which the detector identified a CLC group, a true RonS event was clear in the raw signal, and, as we assumed, the peaks and troughs of the raw signal corresponded with those of the band-pass filtered signal (FIG. 3A1, 2). A false positive was defined as an instance in which the detector identified a CLC group, but a true RonS event was not clear in the raw signal. True negative cases corresponded to sharply contoured inter-ictal discharges without ripples i.e. false RonS (FIG. 3B 1, 2). A true negative was defined as an instance in which the detector identified only sets of CLCs, a ripple was not evident in the raw signal. A false negative was defined as a case in which the detector only identified sets of CLCs when a true RonS was evident in the raw iEEG signal, or alternatively if the trial failed to exhibit an epileptiform discharge. Across all patients, the detectors accuracy was $88.5 \pm 2.1\%$, with a sensitivity of $81.8 \pm 3.4\%$, a specificity of $95.2 \pm 0.81\%$, a precision of $94.5 \pm 1.8\%$, and a negative predictive value of $84.0 \pm 3.9\%$ (s.e.m, n=12). For all the patients, a second reviewer visually validated the detector performance with a Cohen's kappa equal to 0.37, kappa values for individual patients ranged between 0.11-0.6152.

Figure 4:
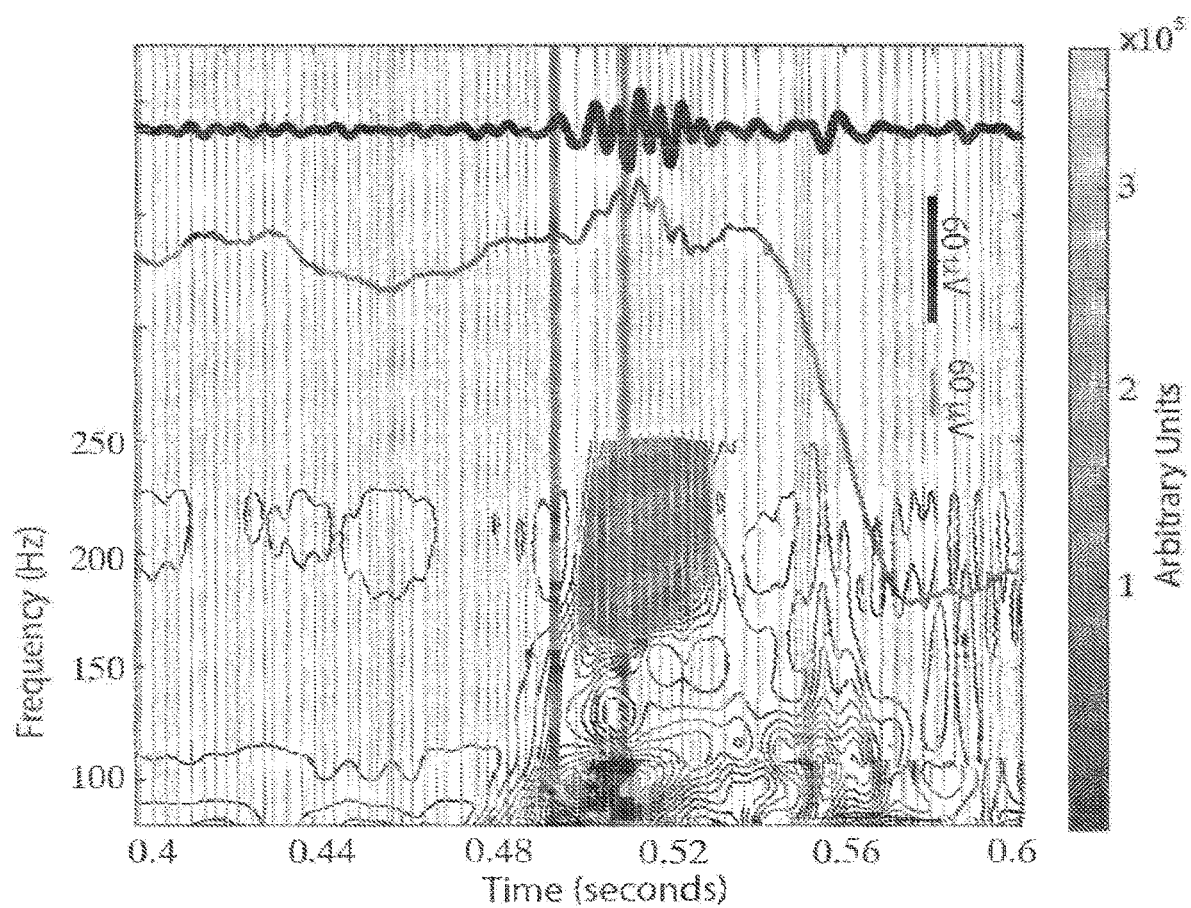
FIG. 4 depicts result of the topographical detection and quantification of distinct ripple and fast-ripple events in human EEG recordings by the method.

Properties of Detected Ripples: We examined the properties of the true RonS events that were identified by the detector and visually verified. For each detected RonS event, the mean power, power-weighted mean frequency, and event duration were quantified. For the combined verified trials, the true RonS had a mean frequency of $109.4 \pm 24.7$ Hz. The detector had the capability of distinguishing fast ripples from ripples, an example of which can be seen in FIG. 4. The true RonS had a mean power magnitude of $47.9 \pm 175.6 * [(10)]^5$ arbitrary units, and a mean duration of $20.5 \pm 12.8$ ms True RonS power magnitude was inconsistent across individual trials, electrodes, and patients. Mean event duration was also variable, but the mean duration corresponded to only two cycles of the mean RonS oscillation period.

Figure 5:
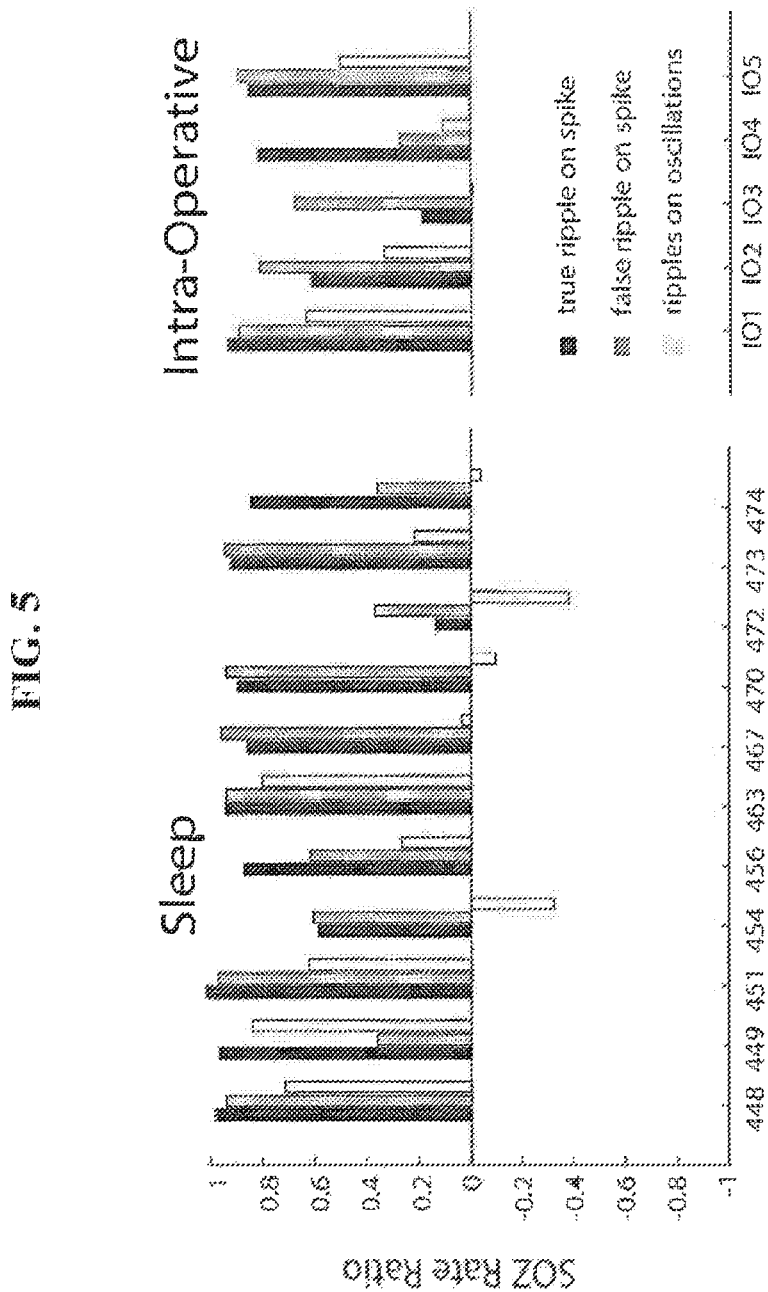
FIG. 5 depicts results of the method applied to human EEG in defining the ratio of ripple on spike and ripple on oscillation events that occur in the seizure-onset zone relative to outside the seizure-onset zone.

Accuracy of the detected ripples for the seizure onset zone: We next addressed whether or not the rates of the different ripple types quantified by the detector could be used to distinguish the SOZ. For all 16 patients, including the five patients with iEEG recordings performed intraoperatively, the mean ripple rates of true and false ripples on spikes recorded inside the SOZ was almost always greater as compared with the non-SOZ (NSOZ), however this was less often the case for ripples on oscillations (FIG. 5). Notably, true and false ripples on spikes were similar with respect to the SOZ rate ratio that compares the mean ripple rate in the SOZ with the mean ripple rate in the NSOZ (n=16, p=0.21, paired t-test, FIG. 4). In contrast, The SOZ rate ratio for ripples on oscillations was decreased with respect to the true ripples on spikes (n=16, p<0.01, paired t-test, FIG. 4A). These differences between the ripple types were also evident in the recordings analyzed in bipolar montage. Overall, the SOZ rate ratios derived from the recordings in referential montage were slightly increased as compared with the SOZ rate ratios derived from the bipolar montage recordings. This difference met statistical significance for the false ripple on spike SOZ rate ratio (paired t-test, n=16 p<0.05). We also generated receiver operating characteristic (ROC) curves for classifying the seizure onset zone on the basis of unscaled ripple rate measurements across all patients in either the sleep, or intra-operative patient cohorts (FIG. 5). Unfortunately, the sample size was too small to address statistical significance of changes in the montage using the ROC methodology. Overall, the classification accuracy of true and false ripple on spike rates for the seizure onset zone was good and the area under the ROC (AUROC) was >76%.

Figure 6:
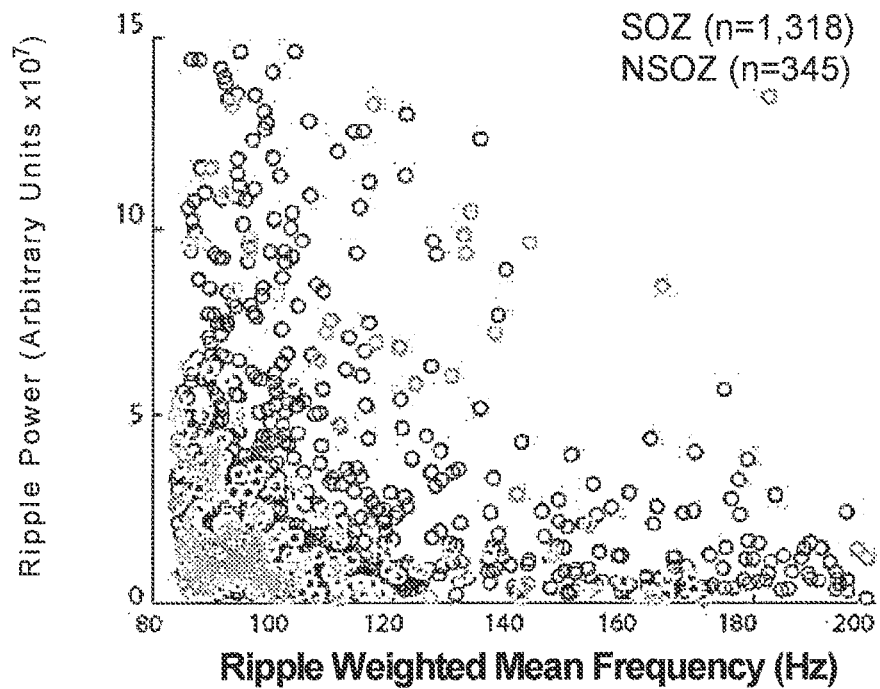
FIG. 6 depicts results of the method applied to human EEG in distinguishing the HFO properties in the seizure-onset zone relative to outside the seizure-onset zone.
Figure 6:
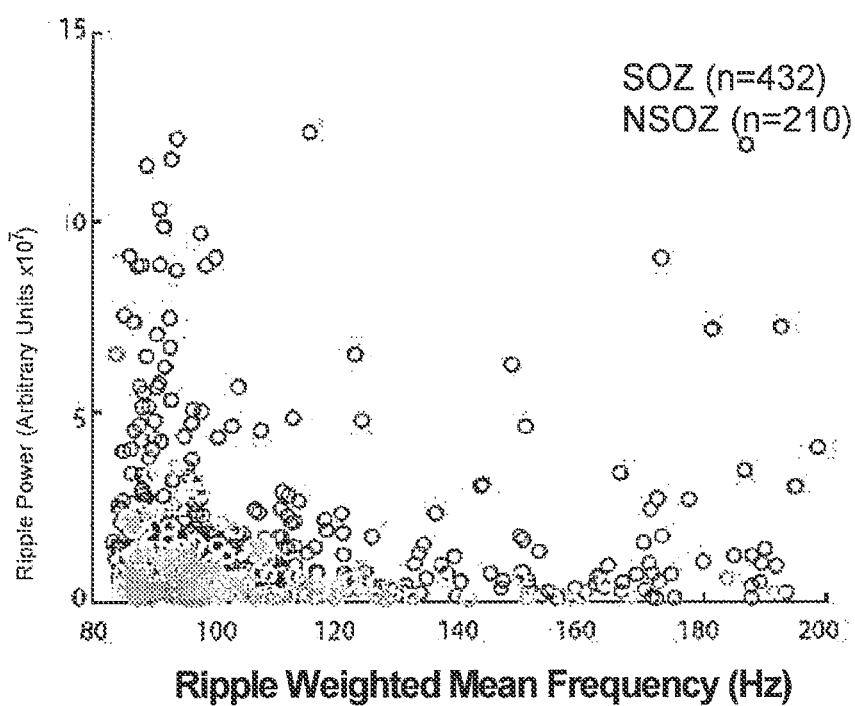
Figure 6:
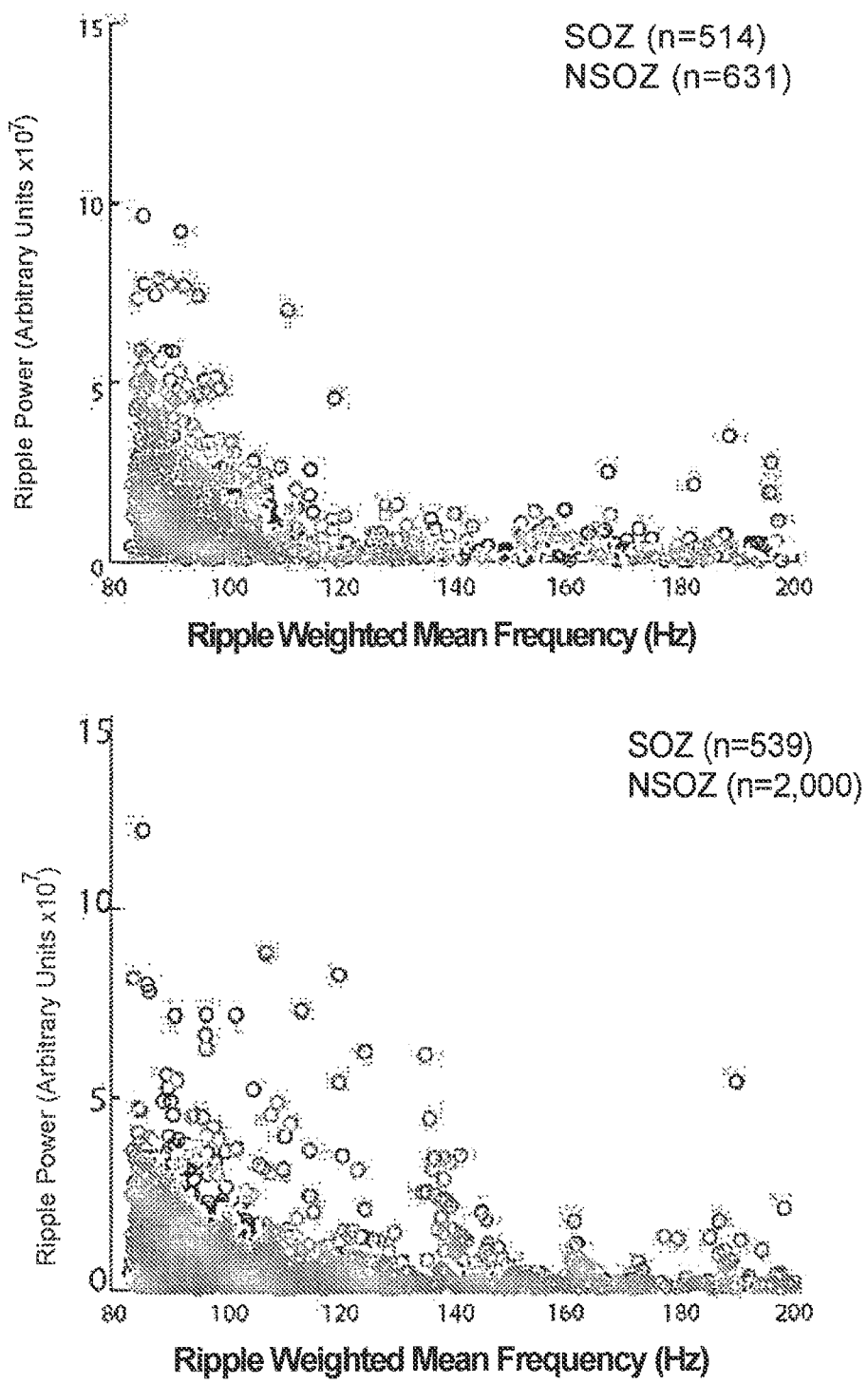

Differences in the spectral content and power of ripples inside and outside the SOZ: We next asked if the properties of ripples, such as spectral content or power, differed depending on whether the event was generated in the SOZ or NSOZ. For true ripples on spikes measured using referential montage it appeared that the events recorded from the NSOZ were of a lower spectral content and lower power as compared with the events recorded from the SOZ. A two-dimensional Kolmogorov-Smirnov test confirmed that the populations or ripple events in the SOZ and NSOZ were distinct when classified by spectral content and power (KS=0.239, p=7.6e-11, FIG. 6). A similar difference was also seen for the events measured during the intra-operative referential montage recordings (KS=0.362, p=3.8e-13, FIG. 6). In contrast, the properties of ripples on oscillations did not strongly depend on whether they were generated in the SOZ or NSOZ (KS=0.167, p=4.3e-5, FIG. 6). The use of bipolar montage recordings reduced the differences between the properties of true ripple on spike events generated in the SOZ as compared with the NSOZ (KS=0.174, p=0.1.3e-5).

Figure 7:
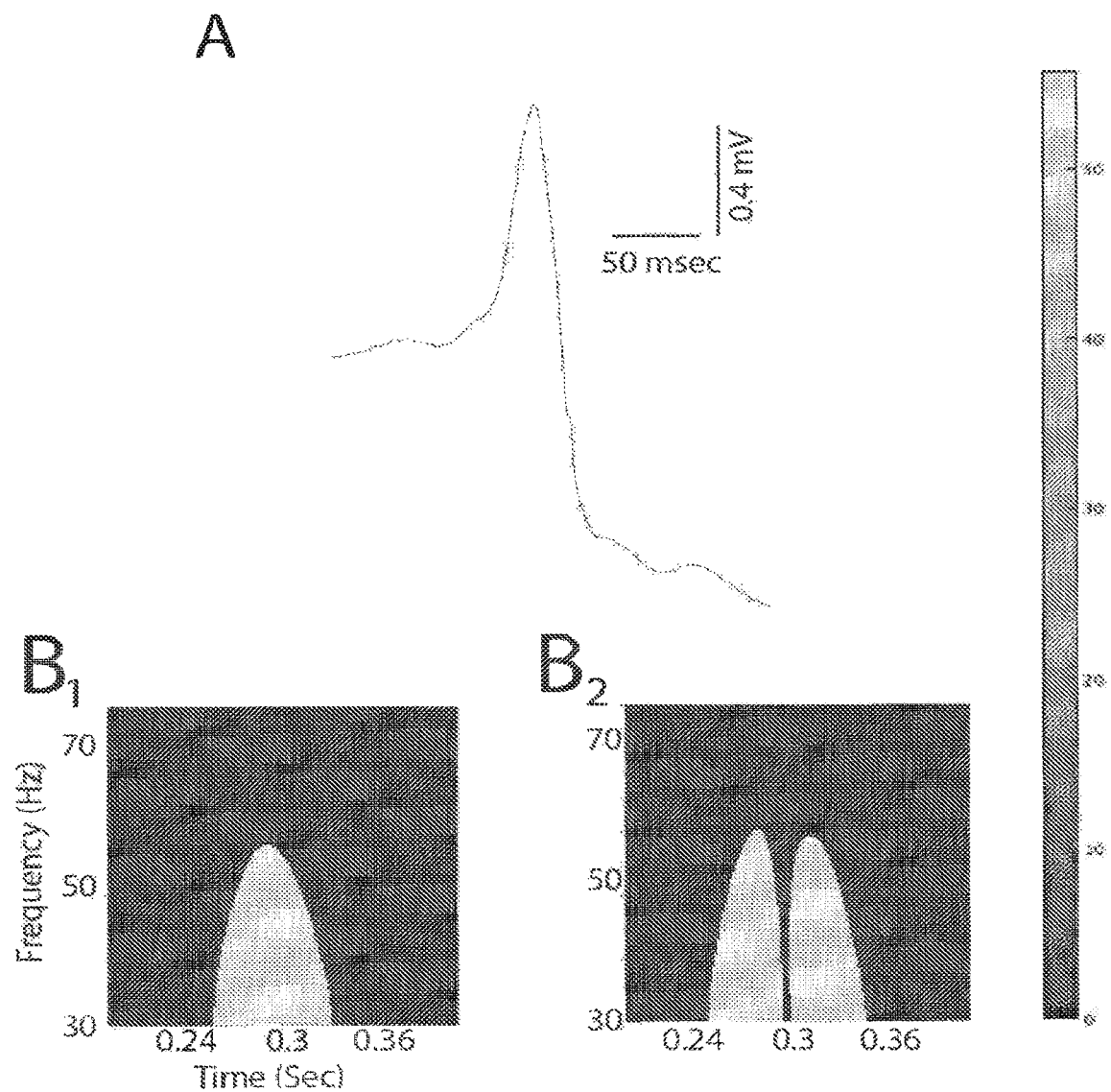
FIG. 7 depicts results of the topographical analysis of the TF plot to detect inter-ictal discharges by the method.

Topographical Identification of Inter-Ictal Discharges: To demonstrate the validity of inter-ictal discharge detection using wavelet convolution and topographical analysis we inspected iEEG recordings annotated by the analysis. We found that across the patients the sensitivity and specificity of inter-ictal spike detection ranged between 80.0-95.9%. FIG. 7A exhibits a EEG tracing with an inter-ictal discharge, FIG. 7B exhibits the corresponding binarized time-frequency plot, and the binarized gradient of the time-frequency plot with the derived borders of the objects shown in grey, FIG. 7C shows the unbinarized time-frequency plot, and gradient of the time-frequency plot in this case the object volumes exceeded the threshold.

Figure 8:
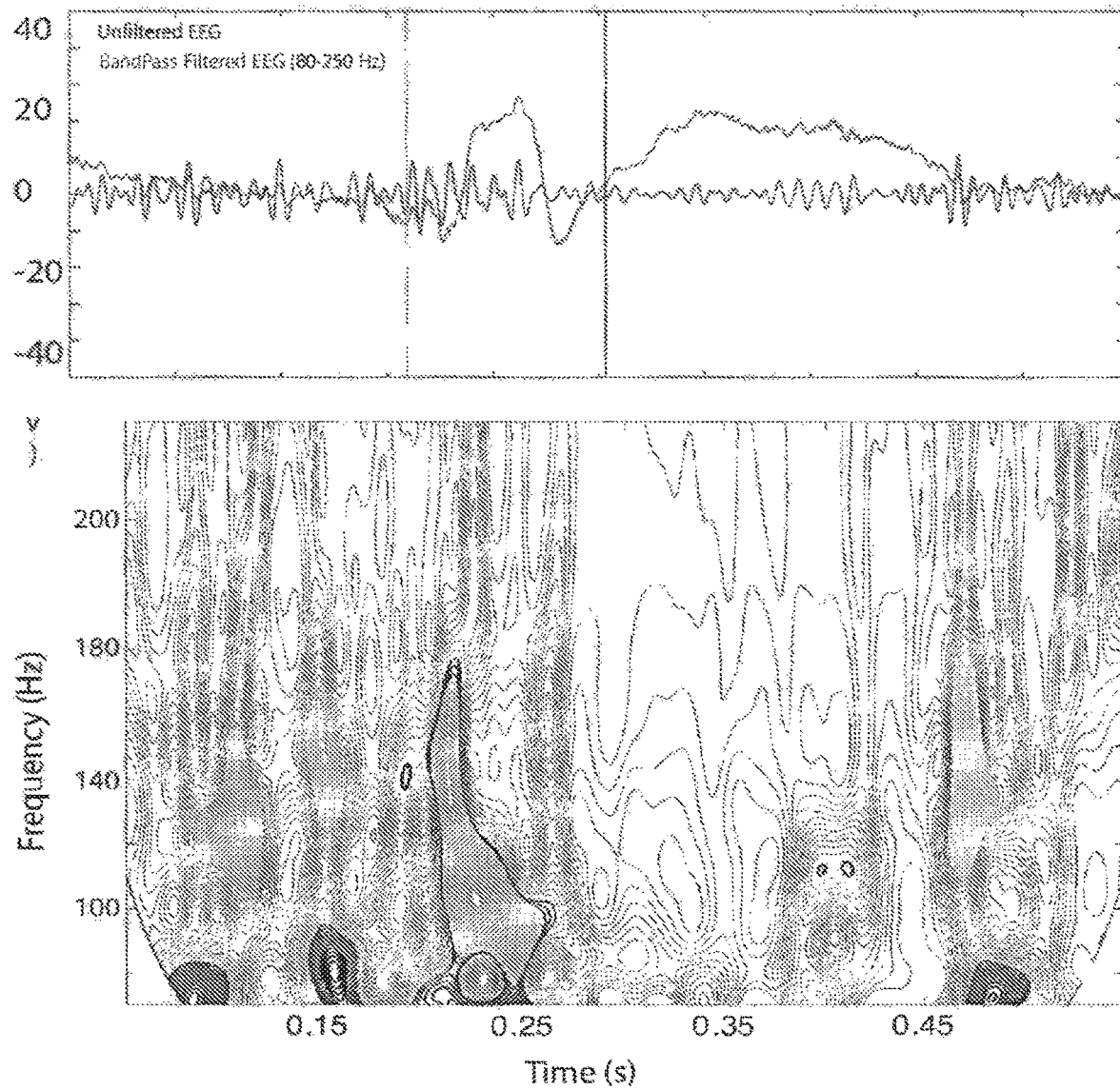
FIG. 8 depicts results of the topographical analysis of the TF plot to identify inter-ictal discharges and ripples on spikes in EEG recordings from the scalp by the method.

Detection of spikes and ripples on spikes in scalp EEG: To demonstrate that the process can be applied both to intracranial EEG and recordings from scalp EEG, in three human scalp recordings with a 2 kHz sampling rate, obtained at Thomas Jefferson University, we first utilized independent component analysis to identify scalp EEG epochs that were not contaminated by artifact (US20150099962A1, WO2017143319A1), we then identified epochs of EEG that were candidate inter-ictal spike events by transforming the recording and using a Debauchies 8 (db8) wavelet, calculating the derivative of the transformed data, and applying a threshold. A second stage of inter-ictal discharge detection utilized the wavelet convolution and topographical analysis (FIG. 8A). If an inter-ictal discharge was detected, we also utilized wavelet convolution and topographical analysis to identify high-frequency oscillations (FIG. 8B).

Figure 9:
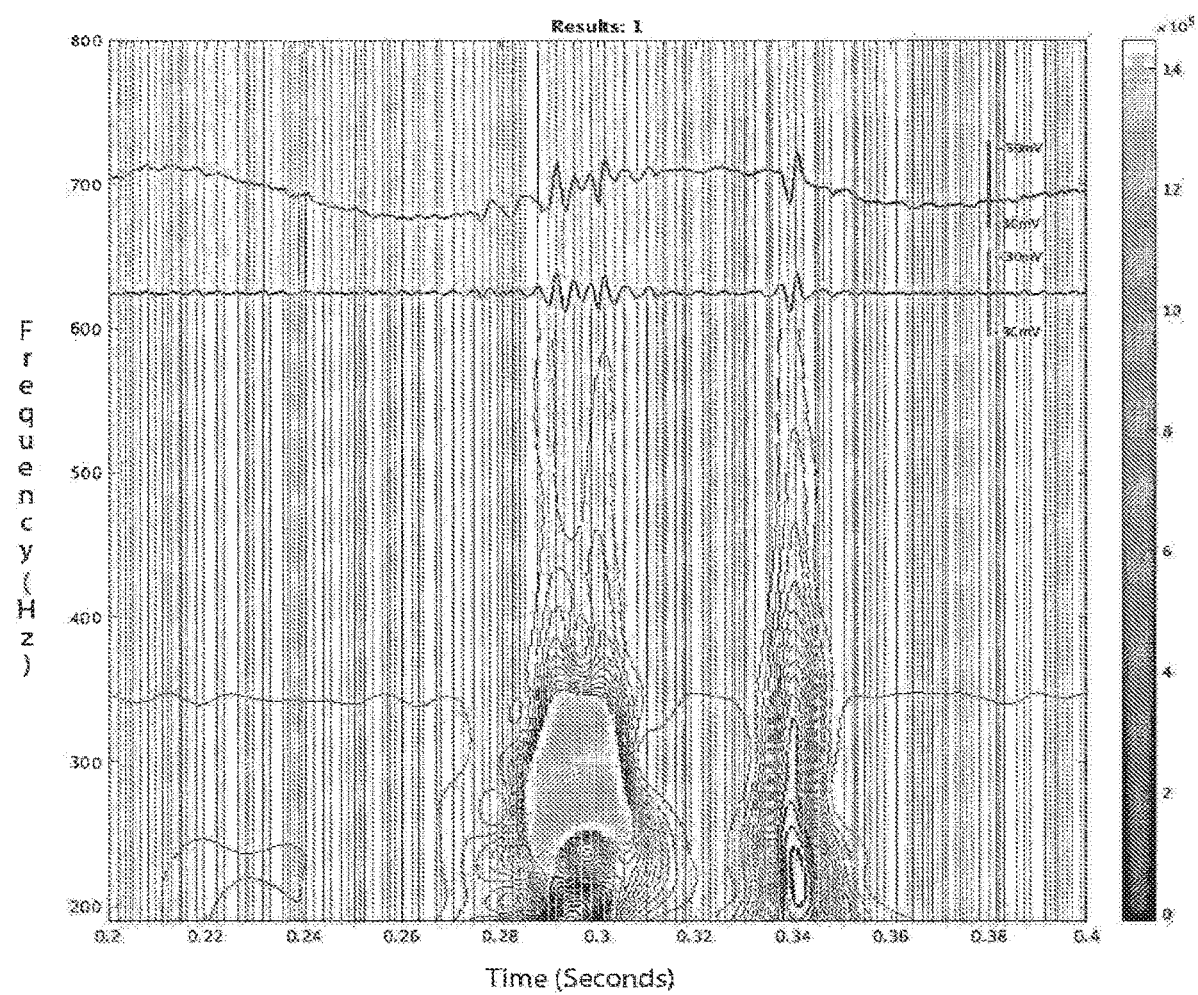
FIG. 9 depicts results of the topographical analysis of the TF plot to detect and quantify a fast ripple used by the method.

Detection of fast ripples in intracranial EEG: Detection of fast ripples in intracranial EEG: Fast ripple detection includes the same process as described above, with certain specifications changed. During the wavelet convolution, complex Morlet wavelets were created with constant frequency domain width of 10, and a Gaussian width of 4 standard deviations. The frequency range of interest is set to 200-600 Hz, so to account for boundary effects, a range of 190-600 Hz is chosen for the initial TF plot. As a proof of concept for the topographical detection of fast ripple oscillations, eighty-eight 600-millisecond clips, which contain possible fast ripple events were analyzed. The clips came from a recording from a patient undergoing intracranial monitoring with depth electrodes, and determined using independent component analysis. Of these clips, fast ripples were detected in 56. The fast ripple oscillations had an average frequency of 260.8±42.8 Hz, a mean power magnitude of $3.86 \pm 6.51*[(10)]^5$, and a mean duration of 21.0±9.3 ms (FIG. 9).

Simultaneous detection of ripples and fast ripples with reflex detection: Simultaneous detection of ripples and fast ripples with reflex detection: During the topographical analysis of the ripple range TF plot, the device may detect open loop contours which begin and terminate at the upper frequency limit of the TF plot. This will trigger a fast ripple reflex detection. A second TF plot is generated in the frequency range of 200-600 Hz, for the entire clip. If a ripple was originally detected, the reflex detection will be focused on the period within 0.1 seconds of the first event, whereas if no ripple event was originally detected, the reflex detection will focus on the period within 0.1 seconds of the peak power coordinate. As a proof of concept of reflex detection we analyzed 9,206 600-millisecond clips containing thought to exhibit ripple oscillations, 118 of these clips triggered reflex fast ripple detections, although no fast ripples were detected.

Classifying ripples on spikes and lower-frequency oscillations during sleep: We categorized the ripple on oscillations in to subtypes using a novel approach. We first applied an optimized Hamming-windowed FIR band-pass filter (eegfiltnew.m; EEGLAB, https://sccn.ucsd.edu/eeglab) to all the iEEG recordings with the following low- and high-pass cutoff values: slow (0.1-2 Hz), delta (2-4 Hz), theta (4-10 Hz), and spindle band (12-16 Hz). We then calculated the instantaneous amplitude of the Hilbert transformed band-pass filtered signals. The instantaneous amplitude was normalized. For each distinct frequency band, we used different minimum amplitude and duration criteria to identify epochs in which oscillatory bursts appeared. The amplitude and duration thresholds for each oscillatory type were adjusted and optimized on the basis of visual inspection of computer annotated iEEG recordings. After identifying the epochs of slow, delta, theta-band, and spindle-band bursts, the time stamps were used to classify the ripple on oscillation in a non-mutually exclusive manner. To examine and quantify phase amplitude coupling, we transformed each ripple event into a ripple phasor, as described in Eqn. 2.

$$ve^{i\theta} = \Sigma_t^T a(t) e^{i\phi(t)} \qquad \text{Eqn. 2.}$$

where v is the vector strength of the phasor, theta its phase angle, and a(t) and ø(t) are the respective instantaneous ripple amplitude or the HFO event power magnitude across the boundary counter and iEEG phase during the ripple across its duration [t . . . T], ø(t) varied depending on whether the ripple was categorized as a ripple on slow wave, delta, theta, or spindle. For each band we calculated a unique instantaneous phase time series ø(t) using a Hilbert transform. Therefore, each ripple event superimposed on two or more, non-mutually exclusive oscillatory activities (e.g., slow and spindle band) resulted in a unique ripple phasor for each band.

Ripple phasor statistical methods: We developed a method to determine whether all the ripple phasors of a given type recorded from a single macroelectrode contact exhibited unimodal or bimodal clustering around preferred, i.e., mean phase angle(s). We used the Circular Statistics Toolbox for Matlab (http://www.mathworks.com/matlab-central/fileexchange/1076-circular-statistics-toolbox-directional-statistics) to test for statistically significant bimodal coupling by performing an agglomerative clustering of the angular data assuming two distributions (circ_clust.m). A criterion for bimodal coupling (i.e., two distinct clusters) was that both clusters had at least 15 members (i.e., angles). We introduced this criterion to increase the probability that the clusters defined by the agglomerative method reflected distinct populations as opposed to outliers. A threshold of 15 angles reflects a ripple event in that distribution occurring approximately every four minutes. We next tested whether the two clusters of phase angles were distinct using the Kuiper's two-sample test (circ_kuipertest.m). If this test met significance ($p<0.05$) the population of phase angles was categorized as bimodal and the mean phase angles of each of the two clusters was recorded. If the Kuiper two-sample test did not meet significance, or the agglomerative method resulted in clusters with less than 15 angles, we combined the clusters and tested for unimodal clustering around a mean phase angle using the Rayleigh test for non-uniformity of circular data (circ_rtest.m). If this test met significance ($p<0.05$) the single mean phase angle defined using (circ_mean.m) was recorded, otherwise the distribution of angles was assumed to be uniform. After calculating the mean phase angle(s) for each electrode we asked if groups of electrodes confined within a neuroanatomical region had a mean phase angle distribution with one (i.e., unimodal) or two clusters (i.e., bimodal). We again used agglomerative clustering and the Kuiper two-sample test ($p<0.05$) for this purpose.

When the two clusters of mean phase angles were statistically distinct, each phase angle was labeled as the following based on their approximate diametrical alignment: the transition from the depth peak to trough (i.e., peak-trough transition) and the transition from the depth trough to peak (i.e., trough-peak transition). If the two clusters of mean phase angles were diametrically opposed between 0° and 180°, then the cluster with the mean phase angle distributed between 0° and 180° was by convention defined as the 'peak-trough transition'. If the two distributions were diametrically opposed between 90° and 270°, then the cluster with the mean phase angle distributed between 90° and 270° was defined as the 'peak-trough transition'. For a single macroelectrode contact, we used the mean and standard deviation of the preferred phase angle of the 'peak-trough transition' category derived from each neuroanatomic region to distinguish the two clusters of phasors. If its preferred phase angle was distributed within the mean and standard deviation of the preferred phase angle, each ripple phasor was categorized as a ripple event occurring during the peak-trough transition. Otherwise, other ripple phasors were categorized as ripple events occurring during the trough-peak transition. We then calculated the incidence ratio for both ripple phasor clusters that compare the relative rate in the SOZ compared to the NSOZ. The clusters were subsequently used to separate the ripple phasors in to two distinct groups corresponding to those that occurred during the depth peak-trough and trough-peak transitions.

HFO-SOZ correlations. We used receiver operating characteristic (ROC) curves (Supporting Information), and a generalized estimated equation (GEE) approach (Supporting Information) to determine if different ripple types during sleep occurred more frequently inside than outside the SOZ.

Figure 10:
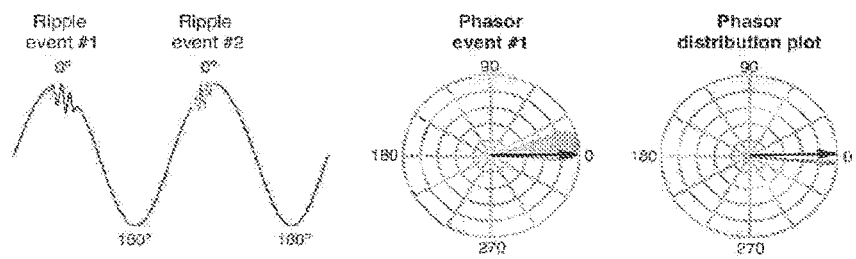
FIG. 10 depicts an illustration of the phase angles of oscillations coupled with ripple events during sleep.
Figure 10:
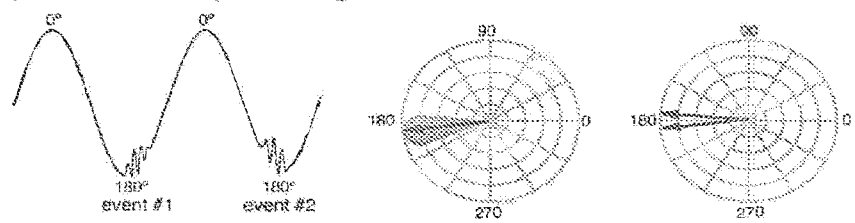
Figure 10:
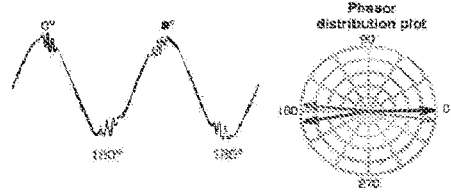
Figure 10:
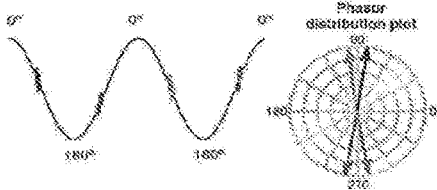
Figure 10:
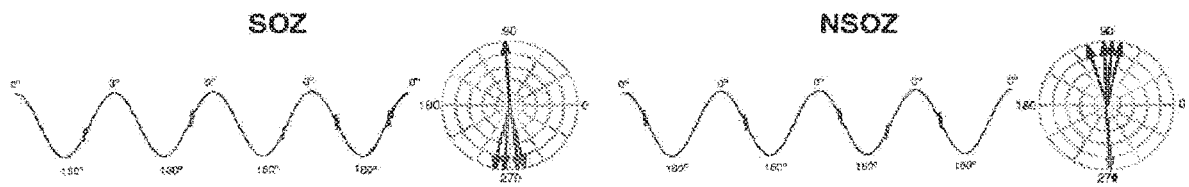

Differentiating pathological and physiological HFOs during sleep. Features of seizures can differ depending on sleep stages as well as the location of seizure onset. Temporal lobe seizures occur more frequently during wakefulness, but frontal and parietal lobe seizures occur more frequently during early non-rapid eye movement (NREM) sleep. Accurate intracranial monitoring is often required when surgery is considered for patients with nocturnal seizures, especially those with the frontal lobe onset. At least three cardinal oscillatory events of NREM sleep may contribute to the local and global neural changes that drive epileptogenesis: slow, spindle, and ripple oscillations. Slow oscillations (~0.75 Hz) consisting of alternating phases of the hyperpolarized/down- and depolarized/up-state, involves cortical and thalamic networks. Spindle-band oscillations (12-16 Hz) are generated by smaller local networks of thalamic and cortical neurons, and are often phase-locked to slow oscillations during slow-wave sleep. Ripples, defined as brief bursts (~50-150 msec) of high-frequency (80-200 Hz) neurophysiological activity, are highly synchronized local network events that occur concurrently with slow waves, and sleep spindles. In humans with neocortical epilepsy, ripple rates can be increased primarily in the seizure-onset zone (SOZ), but sometimes also in the non-SOZ (NSOZ). Ripple events occur during both the transition between the down-up state, and the up-down state of slow waves. Thus, ripple amplitude can be considered coupled with slow wave phase at two preferred phase angles. The ripples coupled to one preferred phase angle (i.e., down-up state) may be physiological, and the ripples coupled to the other preferred phase angle (i.e., up-down state) may be pathological (FIG. 10). In accord with this notion, the ripple events that occur during the up-down transition are generated more frequently in the SOZ. Also, intracranial EEG (iEEG) recordings from human hippocampus contralateral to the SOZ have demonstrated that ripple events that occur during the down-up transition are likely physiological because they are nested in the trough of spindle oscillations, and may mediate memory consolidation. In principle, a method that can distinguish putative pathological from physiological ripples should be able to distinguish two clusters of ripple events. One of these clusters should exhibit elevated rates selectively in epileptogenic regions, relative to the other cluster. This technique was used to distinguish putative physiological and pathological ripples coupled with slow waves. It is not yet clear if this method can be applied to ripples that occur superimposed on other sleep oscillations. To determine if coupling between ripple amplitude and the phase of delta, theta, and spindle sleep oscillations could help distinguish physiological ripple events from pathological ripple events, we 1) examined the relationship between the phase of the distinct oscillations composing core sleep architecture and the amplitude of ripple events, 2) defined two distinct populations of ripples based on the preferred phase angle of coupling, and 3) tested whether one of the populations had a higher incidence ratio in the SOZ (FIG. 10).

Figure 11:
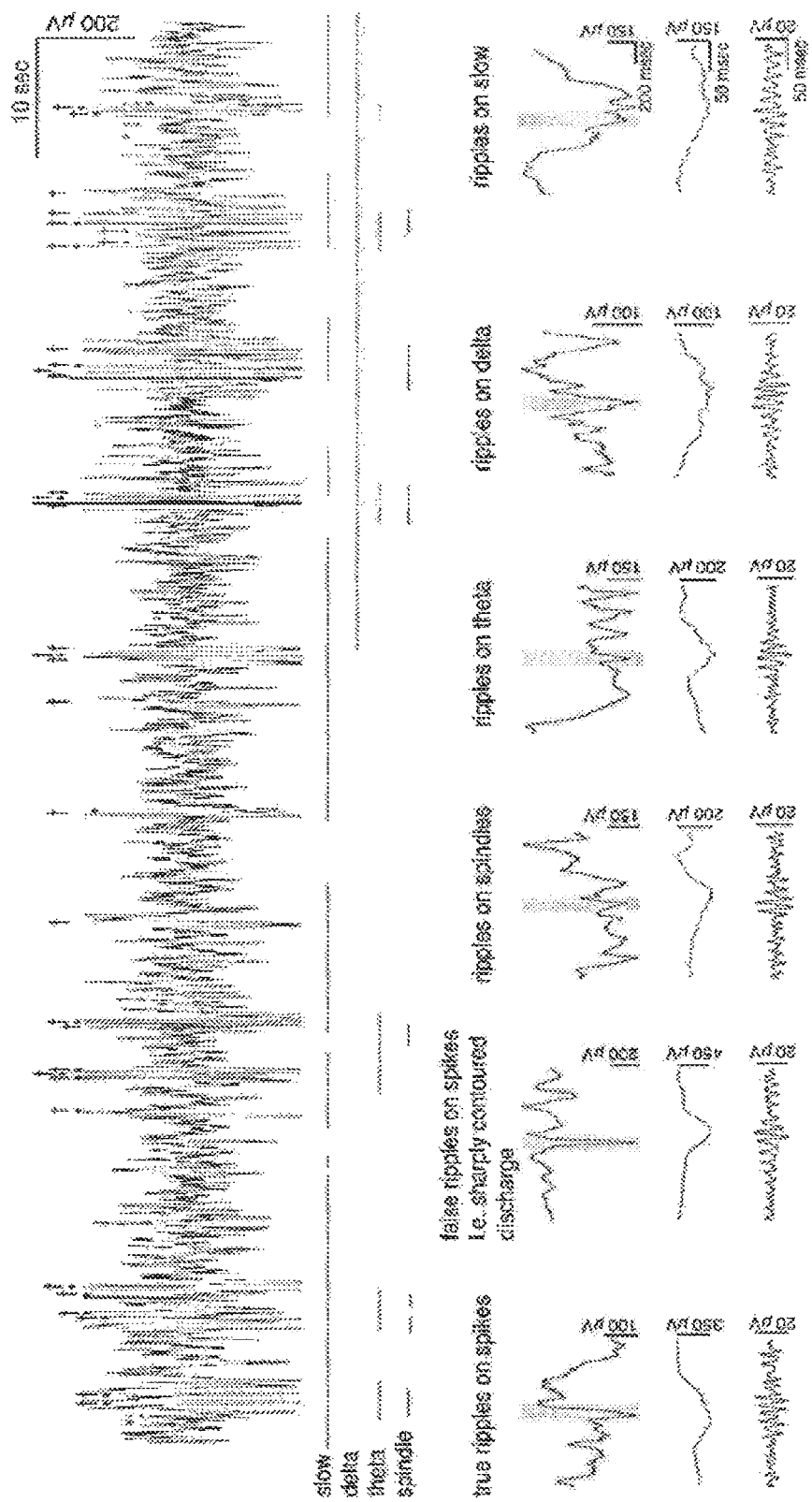
FIG. 11 depicts an illustration of the detection of oscillatory bursts and the classification of ripples using a defined taxonomy used by the method.
Figure 12:
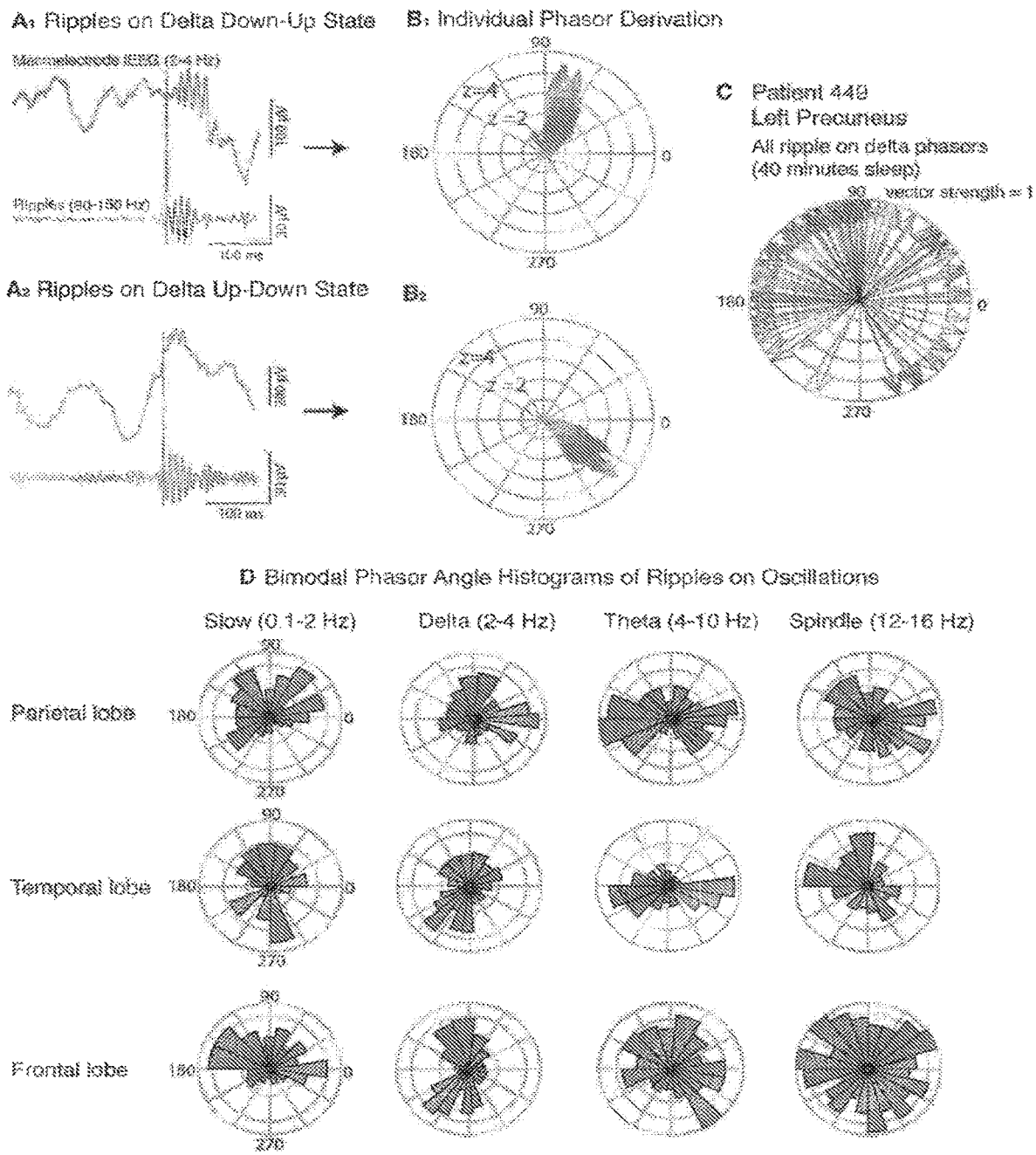
FIG. 12 depicts an example of the derivation of ripple phasors, and the identification of a bimodal distribution of the preferred phase angle of coupling in defined neuroanatomical regions used by the method.
Figure 13:
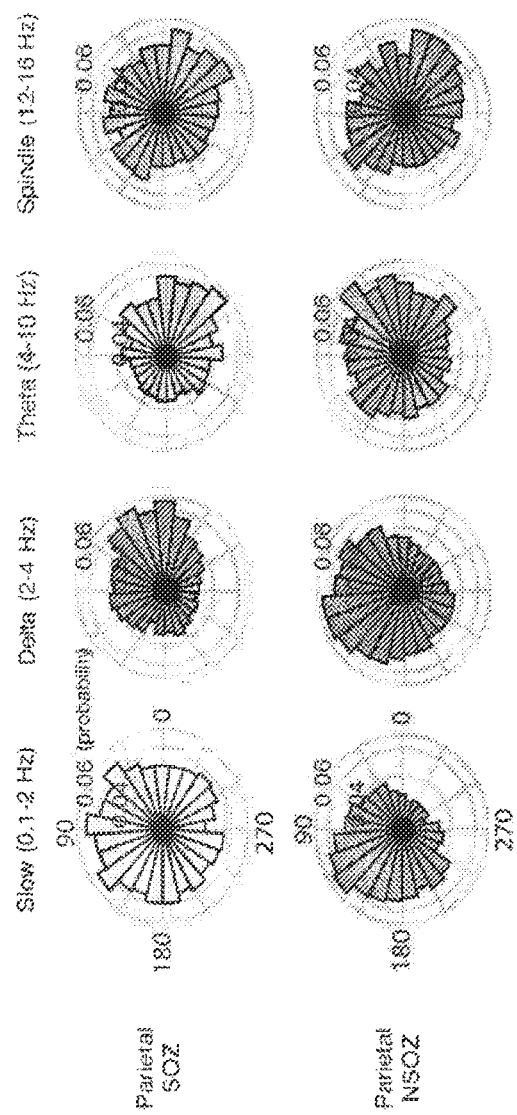
FIG. 13 depicts an example of the distinction of the seizure-onset zone, and non-seizure onset zone in the parietal lobe of patients with neocortical epilepsy based on the preferred phase angle of coupling used by the method.
Figure 14A:
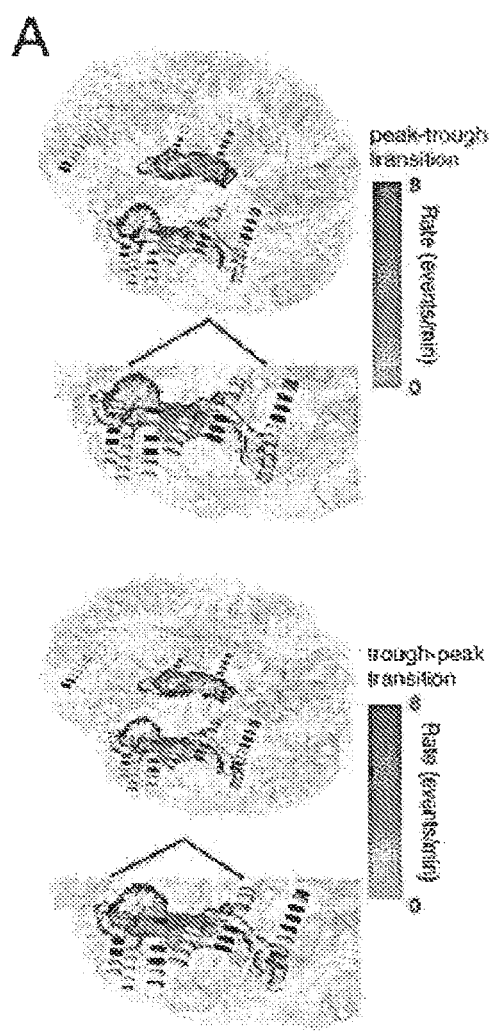
FIGS. 14A and 14B depict incidence ratio of ripples occurring in the peak-trough or trough-peak distribution in the seizure onset zone used by the method.
Figure 14B:
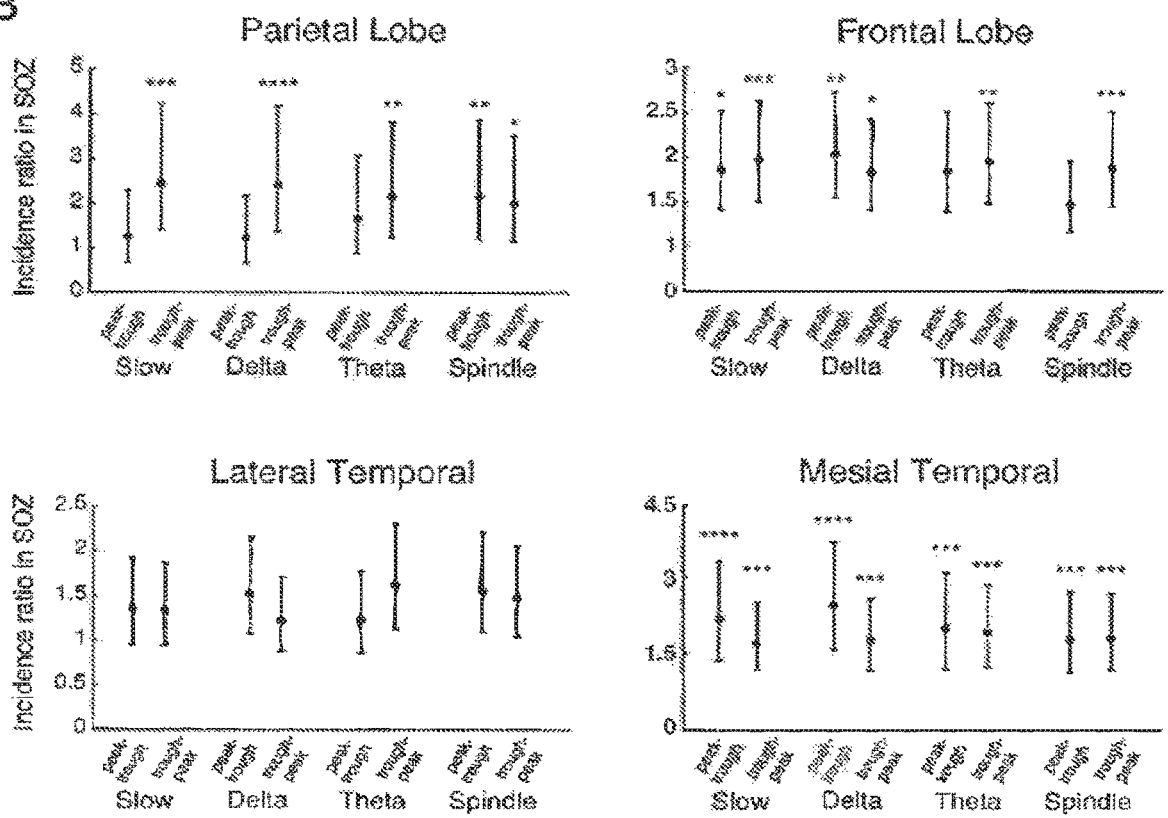
Figure 15:
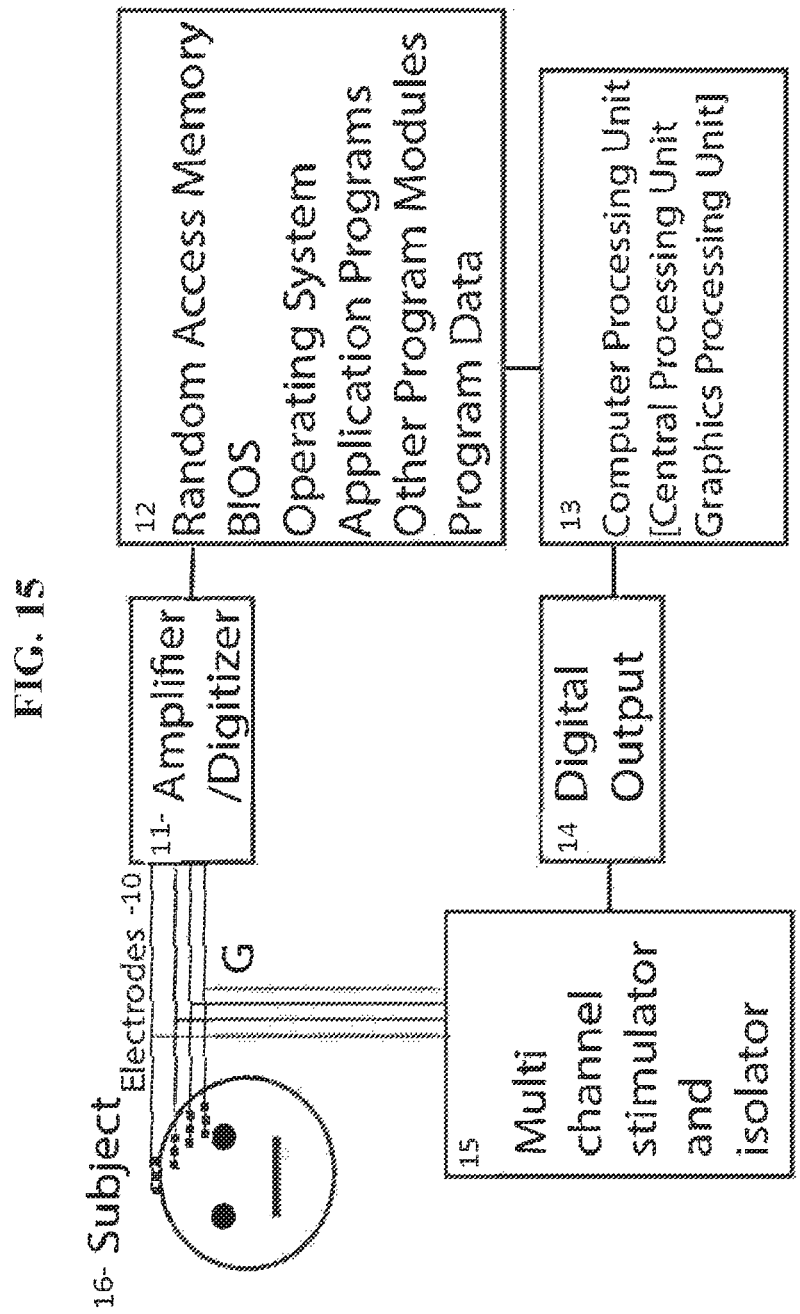
FIG. 15 depicts a diagram of the a device for capturing electrical signals from the brain suitable for performing an embodiment of the method described herein.

Coupling between oscillatory phase and ripple event amplitude during sleep: We selected depth electrode intracranial EEG (iEEG) recordings from patients with focal-onset seizures. Nine patients had mesial temporal lobe epilepsy (MTLE; 7 unilateral, 2 bilateral), seven patients had mesial temporal and neocortical lobe epilepsy (MTLE+), and seven patients had neocortical epilepsy (NEO) (Supplementary Table 1). Among the 14 patients with neocortical SOZs, eight patients had SOZ sites located in the lateral temporal lobe, five patients had SOZ sites located in the frontal lobe, and six patients had SOZ sites located in the parietal lobe. We analyzed iEEG recordings ranging from between 7-17 depth electrodes with 7-16 macroelectrode contacts per patient. We detected a total of 207,175 inter-ictal ripples, which occurred superimposed on either epileptiform spikes or normal sleep architecture (FIG. 11). We utilized ripple phasors that relate the phase of each lower-frequency oscillation to the amplitude of each ripple event (FIG. 12A-B). As shown in FIG. 12C, polar plots of the population of delta ripple phasors identified in a single, neocortical depth electrode during the entire recording epoch often demonstrated two clusters of ripple phasor angles (i.e., a bimodal distribution). A bimodal distribution of ripple phasor angles recorded from a single macroelectrode was not only observed in the case of delta ripple phasors, but also for slow, theta, and spindle ripple phasors. We next asked whether the preferred phase angle(s) of ripple coupling were consistent across multiple recording sites confined to an anatomical region. When we pooled all the mean phase angles across all the recording sites confined within each anatomical region, we found that the distribution of these mean phase angles was also bimodal (i.e., two distinct clusters, FIG. 12D; Kuiper's V-test, $p<0.05$). Overall, most ripple events occur during either the peak-trough or the trough-peak transition of slow, delta, theta, and spindle band activity. In the few cases that the mean preferred phase angles occurred around the trough of an oscillation, these ripple events were labeled as the 'peak-trough transition', whereas if the preferred phase angles occurred during the peak of an oscillation, the events were labeled as the 'trough-peak transition'. Distinct couplings between sleep oscillatory phase and ripple event amplitude in and outside the SOZ. We asked if the preferred phase angle of coupling between oscillatory phase and ripple event amplitude during sleep differed in the SOZ as compared with the NSOZ. In the absence of an a priori assumption regarding the distribution of ripple phasor angles, we still observed differences between phase-event amplitude coupling in the SOZ and NSOZ. In the parietal lobe, there was a statistically significant difference in the distribution of ripple phasor angles detected in the SOZ as compared with the NSOZ for all oscillatory types coupled with ripple events. The distinction was strongest for ripples on delta ($k=1.71E+06$, $p=0.001$) (FIG. 13). We also observed statistical differences for other ripple types in other neuroanatomical locations. When it was assumed that ripple event amplitude could be coupled with oscillatory phase around two preferred phase angles (i.e., two clusters), the relationship between the preferred phase of ripple coupling and the location of the SOZ could be better quantified (FIG. 14). The incidence ratio of ripples occurring during the peak-trough transition of slow oscillations was not significant in the parietal lobe ($p=0.494$), or did not reach significance in the frontal lobe after correction for multiple comparisons ($p=0.024$). However, the incidence ratio of ripples occurring during the trough-peak transition of slow oscillations was significant in both the parietal ($p=0.001$) and frontal lobe SOZ ($p=0.004$). The effect size was larger in the parietal lobe as compared with the frontal lobe. We observed a similar distinction for ripples occurring during the peak-trough and trough-peak transition of delta and theta band activity in the parietal lobe. In the frontal lobe, the incidence ratio of ripples occurring during the peak-trough ($p=0.002$) and trough-peak transition ($p=0.019$) were both significant, but for theta ($p=0.006$) and spindle ($p=0.009$) ripples only the incidence ratio of ripples occurring during the trough-peak transition was significant. In frontal and parietal lobe SOZ, the increased incidence ratio of ripples occurring during the trough-peak transition of oscillations was observed from a majority of patients, and also in the resected region for two neocortical epilepsy patients who were seizure free following surgery. Neither cluster of ripple phasors was increased in rates selectively for the SOZ located within the lateral temporal lobe (all $p>0.09$), whereas both clusters of ripple phasors were increased in rates in the mesial temporal SOZ relative to NSOZ (all $p<0.005$). We also asked if macroelectrode contacts in SOZ sites more often exhibited a bimodal distribution (i.e., two clusters) of preferred ripple phasor angles, as compared with macroelectrode contacts in NSOZ sites. We found that in the parietal lobe, and to a lesser extent the frontal lobe, a greater proportion of recording sites in the SOZ exhibited a bimodal as opposed to a unimodal distribution (i.e., one cluster) of ripple phasor angles.

The report generated by the method includes the electrode locations or identifiers and the HFOs that occurred at each of these locations. Specifically, the report includes the onset and offset times of the HFO, the HFO category, and the HFO properties such as frequency, duration, power, and the phase angle of the corresponding phasors. The report can be used to generate annotations of the EEG record. The annotated EEG can be visually interpreted by a clinician to guide clinical decision making, and a therapeutic procedure such as; [1. resective or thermally ablative epilepsy surgery, 2. gene therapy, 3. cell therapy, 4. or the placement of a device that stimulates the brain with electricity or optogenetic stimulation] can be selected and targeted on the basis of the human visual inspection of the computer annotated EEG record. The report generated by the method can also include, for each and every HFO event detected during a defined epoch, the HFO classification, HFO properties, and the probability that an HFO is of pathological or physiological origin on the basis of the HFO phasor analysis. This report can be presented to the clinician or another software process, in the absence of the original EEG record, to target a therapeutic procedure such as resective or thermally ablative epilepsy surgery, gene therapy, cell therapy, or the placement of a device that stimulates the brain with electricity or optogenetic stimulation.

The preferred embodiment is a device composed of a) a subject with a plurality of electrodes 10; b) a brain signal acquisition device (Amplifier/digitizer) 11 to record electrical signals from multiple locations of a subject; c) a non-transitory computer-readable memory storing instructions executable 12 by the computer processor 13; d) a computer processor 13; e) digital outputs 14; f) a multichannel stimulator 15; and g) a subject 16 with a plurality of brain stimulating electrode(s). The computer processor; and a non-transitory computer-readable memory storing instructions executable by the computer processor; are configured to execute the method applied to the brain signals recorded by the plurality of the electrodes, for example include the RAM, BIOS, an operating system, application programs, program data, and other program modules as necessary to implement and run the system. The report generated by the method is translated by the computer processor and computer-readable memory in to a train of TTL pulses transmitted by the digital output. A multichannel stimulator connected to the digital output reads the TTL pulses and electrically stimulates the brain by generating current that is transmitted via the brain stimulating electrode.

The required features of the preferred embodiment are that the device can stimulate brain region(s) with therapeutic regimens to reduce seizures, and can also stimulate brain region(s) with therapeutic regimens to enhance memory. The selection of the regimen of brain stimulation used by the preferred embodiment is dependent on whether the purpose of the stimulation is to reduce seizure occurrences and abort seizures, or alternatively enhance memory. The report generated by the method identifies, classifies, and quantifies each HFO and determines the associated probability of each HFO resulting from a physiological process involved with memory and cognition, or a pathophysiological process involved with epilepsy based on the HFO type, HFO properties, and a comparison of the HFO phasor's phase angle with a probability density functions of phase angles derived from EEG and local field potential recordings from healthy human brain areas, healthy primate brain areas, and epileptogenic brain areas in patients with epilepsy. Thus, the report generated by the method can be utilized by the preferred embodiment to determine when and where a brain area is engaged in memory related activity, or alternatively engaged in pathophysiological activity associated with epilepsy or epileptic seizures. The preferred embodiment can comprise a device that is worn or implanted in the patient. Also, in another embodiment, the digital output from the system can trigger an environmental stimulus such as an audio or visual alert that warns the subject of an impending seizure.

What is claimed is:

1. A non-transitory computer readable medium storing instructions that, when executed by a processor, are configured to identify brain electrical activity displaying of a predefined HFO duration, HFO mean power, HFO mean frequency, and HFO phasor were recorded by:
    receiving electrical signals recorded from multiple locations in the brain of a subject using an electrical signal sensing device;
    filtering the electrical signals to produce a high frequency oscillation (HFO) data stream and a low-frequency data stream;
    applying independent component analysis to the HFO data stream and removing noise from the HFO data stream;
    determining the location of HFO events in the HFO data stream;
    applying a wavelet convolution to the electrical signals at the location of HFO events to generate a time-frequency representation of the power of the signal;
    determining a region of this first time-frequency plot that exceeds a threshold; wherein if the threshold is not met no HFO is registered by the apparatus;
    determining the topography of a second time-frequency plot temporally centered around suprathreshold region of the first time-frequency plot by identifying contours of isopower;
    determining at least two vertices of each contour as a coordinates of time and frequency;
    determining which contours exceed a specified threshold, and excluding all other contours;
    determining each contour as open-loop or closed-loop based on the coordinates of the vertices;
    determining groups of contours based on their open- or closed-loop classification, power level, and time-frequency coordinates;
    determining an event boundary contour as the closed loop contour of lower isopower in the group that exceeds a threshold value;
    determining new event boundary coordinates by generating a third time-frequency plot with a lower minimum frequency limit than the second time-frequency plot and recalculating the event contours and contour group, if the minimum frequency of the original boundary contour is below a predetermined threshold;
    determining a duration of the HFO event based on the event boundary contour;
    determining a mean power of the HFO by calculating the mean power magnitude across all coordinate points of the time-frequency plot within the event boundary contour;
    determining an amplitude-weighted mean frequency of the HFO even within the boundary contour;
    determining if there are open loop contours that begin and terminate at the upper frequency limit of the second time-frequency plot;
    determining if these open loop contours are representative of a second HFO event by calculating a fourth time-frequency plot in a higher frequency range, identifying the region of greatest power that exceeds a threshold, defining contours of isopower, determining if these are open or closed loop contours, defining groups of contours, and determining the even boundary contour;
    applying a distinct wavelet convolution to the electrical signals to generate a time-frequency representation of the power of the signal in a frequency range less than the HFO to determine if the HFO event is superimposed on an inter-ictal discharge, or if an inter-ictal discharge has a superimposed HFO by performing a wavelet convolution to the electrical signals to generate a time-frequency representation of the power of the signal (TF plot);
    determining the gradient plot of this TF plot; by calculating both the horizontal gradient of the TF plot, $$\nabla P_t = \frac{\partial(\text{power magnitude})}{\partial(\text{time})};$$

and the vertical gradient of the TF plot, $$\nabla P_f = \frac{\partial(\text{power magnitude})}{\partial(\text{frequency})};$$

and combining these two gradients as, $$\nabla TF_{map} = \sqrt{(\nabla P_f)^2 + (\nabla P_t)^2};$$

determining the borders of objects in the TF plot, and the gradient plot of the TF plot, discharges by binarizing the TF plot and its gradient using an appropriate threshold and applying Moore-neighbor tracing algorithm;
    determining the volume of the objects in the TF plot, and the gradient plot of the TF plot, using trapezoidal surface integration within the object borders derived from the binarized TF plot to the unbinarized TF plot, and gradient plot of the TF plot;
    determining if any of the objects are near the borders of the TF plot, or have a height-width ratio less than a threshold and excluding these object from further analysis;

determining if an object is representative of an inter-ictal discharge by defining the object of greatest volume in the TF plot, and object of greatest volume in the gradient plot of the TF plot, and calculating if the volume of these objects exceeds pre-defined thresholds;

filter the electrical signals recorded from multiple locations of a subject using an electrical sensing device to produce a low-frequency data stream to determine if the preferred phase angle of coupling between the HFO and bursts of slower oscillations;

transform the low-frequency data stream to produce a low-frequency instantaneous phase; and instantaneous amplitude;

determining the start and end times of oscillatory bursts by smoothing the instantaneous amplitude function and applying predetermined thresholds;

determining if the HFO coincides with one or several oscillatory burst epochs;

determining an HFO phasor with a mean phase angle and vector strength value based on the low-frequency burst instantaneous phase and the mean HFO event power magnitude across the boundary counter;

determining the probability that a HFO resulted from either a process involved with memory and cognition, or a pathophysiological process involved with epilepsy on the basis of a comparison of the HFO duration, HFO mean power, HFO mean frequency, and HFO phasor with a pre-existing database of the values of these parameters;

identifying a location of the brain corresponding with the same electrical signals determined to displays HFOs of a predefined HFO duration, HFO mean power, HFO mean frequency, HFO phasors, and pathological HFO probability, based on where the electrical signals were recorded;

generating a report of the identified location of the subject as a target for a therapeutic procedure for treating a cause of the identified HFO events; and performing a therapeutic procedure based on the identified report of brain activity displaying HFOs of a predefined HFO duration, HFO mean power, HFO mean frequency, and HFO phasors;

wherein the therapeutic procedure comprises one or more procedures selected from a group of procedures consisting of surgical resection of a portion of the brain or a lesion thereon, laser ablation of a portion of the brain or a lesion thereon, targeted gene therapy of a portion of the brain, cell therapy targeting a portion of the brain, and implanting a therapeutic device in the brain.

2. The non-transitory computer readable medium of claim 1, wherein the electrical sensing device is a non-invasive or minimally invasive electroencephalogram.

3. The non-transitory computer readable medium of claim 1, wherein the electrical sensing device is an intracranial electroencephalogram.

4. The non-transitory computer readable medium of claim 1, wherein the location corresponds with epileptogenic brain.

5. The non-transitory computer readable medium of claim 1, wherein the location corresponds with brain wherein pathological activity interferes with cognitive function and memory.

6. The non-transitory computer readable medium of claim 1, wherein the location corresponds with brain actively encoding, consolidating, or recalling memory.

7. The non-transitory computer readable medium of claim 1, further comprising identifying, in the generated report, a neurological or psychiatric illness associated with the identified location.

8. The non-transitory computer readable medium claim 1, wherein further comprising recording electrical signals using a plurality of recording electrodes situated at multiple locations relative to the brain of the subject.

* * * * *